United States Patent
Thomssen et al.

(10) Patent No.: US 8,210,847 B2
(45) Date of Patent: Jul. 3, 2012

(54) DISPOSABLE DENTAL HANDPIECE

(75) Inventors: Eli Thomssen, Kalamazoo, MI (US);
Dirk Schipper, Kalamazoo, MI (US);
Kevin Turner, Highland Village, TX (US)

(73) Assignee: Axenic Dental, Inc., Kalamazoo, MI (US)

( * ) Notice: Subject to any disclaimer, the term of this patent is extended or adjusted under 35 U.S.C. 154(b) by 463 days.

(21) Appl. No.: 12/200,724

(22) Filed: Aug. 28, 2008

(65) Prior Publication Data
US 2009/0061384 A1    Mar. 5, 2009

Related U.S. Application Data

(60) Provisional application No. 60/969,094, filed on Aug. 30, 2007.

(51) Int. Cl.
*A61C 1/05* (2006.01)
*A61C 1/08* (2006.01)

(52) U.S. Cl. .................. 433/132; 433/126; 415/904

(58) Field of Classification Search ........... 433/114, 433/115, 125, 126, 127, 132, 133; 415/904
See application file for complete search history.

(56) References Cited

U.S. PATENT DOCUMENTS

| | | |
|---|---|---|
| D110,936 S | 8/1938 | Wiseman |
| D121,506 S | 7/1940 | Davis |
| D162,002 S | 2/1951 | Brown |
| D174,181 S | 3/1955 | Howie |
| 3,120,705 A | 2/1964 | Hoffmeister et al. |
| 3,189,999 A * | 6/1965 | Reiter .............................. 433/82 |
| 3,310,285 A * | 3/1967 | Hawtin .............................. 415/1 |
| 3,418,715 A * | 12/1968 | Ellis .............................. 433/126 |
| 3,552,021 A | 1/1971 | Graceffo et al. |
| D219,979 S | 2/1971 | Coss |
| 3,589,828 A * | 6/1971 | Mosimann .................... 415/112 |
| 3,727,313 A | 4/1973 | Graham |
| 3,893,242 A | 7/1975 | Lieb et al. |
| D239,390 S | 3/1976 | Webb |
| 3,946,490 A | 3/1976 | Sotman et al. |
| 3,955,284 A | 5/1976 | Balson |
| D241,550 S | 9/1976 | Morin |

(Continued)

FOREIGN PATENT DOCUMENTS

CH    686113 A5    1/1996

(Continued)

OTHER PUBLICATIONS

Supplementary European Search Report to European Application No. 04 72 0427, dated Apr. 5, 2007 listing documents cited.

(Continued)

*Primary Examiner* — John J Wilson
(74) *Attorney, Agent, or Firm* — Honigman Miller Schwartz and Cohn LLP

(57) ABSTRACT

A sterile, substantially maintenance free disposable dental handpiece is constructed from two shells and a center core, the center core having a flow deflector on one end. The shells are joined around the core with mating protrusions and/or tapered walls to form the body and head of the handpiece. A base is integrally-formed with the center core. The base has conduits that allow entry of light and pressurized air and/or water into the body. The head at the opposite end of the body from the base rotatably mounts an impeller assembly having an impeller shaft. The impeller shaft includes blades driven by the pressurized air. The blades can have cavities to reduce weight.

10 Claims, 20 Drawing Sheets

U.S. PATENT DOCUMENTS

| | | | |
|---|---|---|---|
| 4,014,099 A | 3/1977 | Bailey |
| D251,304 S | 3/1979 | Leonard |
| D254,570 S | 3/1980 | McDonald |
| D255,929 S | 7/1980 | Austin, Jr. |
| D255,930 S | 7/1980 | Nilles et al. |
| D257,284 S | 10/1980 | Leonard |
| 4,249,896 A | 2/1981 | Kerfoot |
| D261,032 S | 9/1981 | Marucci et al. |
| D261,301 S | 10/1981 | Marucci et al. |
| D263,877 S | 4/1982 | Podszus et al. |
| D264,876 S | 6/1982 | Seid |
| D267,036 S | 11/1982 | Podszus et al. |
| 4,370,132 A | 1/1983 | Wohlgemuth |
| D269,122 S | 5/1983 | Seeley |
| 4,406,470 A | 9/1983 | Kataoka et al. |
| 4,661,060 A | 4/1987 | Strohmaier |
| 4,795,343 A | 1/1989 | Choisser |
| 4,842,516 A | 6/1989 | Choisser |
| D305,935 S | 2/1990 | Straihammer et al. |
| 4,941,828 A | 7/1990 | Kimura |
| 4,978,297 A | 12/1990 | Vlock |
| 5,007,831 A | 4/1991 | Bierbaum et al. |
| 5,028,233 A | 7/1991 | Witherby |
| 5,040,978 A | 8/1991 | Falcon et al. |
| 5,096,421 A | 3/1992 | Seney |
| 5,156,547 A | 10/1992 | Bailey |
| 5,160,263 A | 11/1992 | Meller et al. |
| D335,347 S | 5/1993 | McKeown |
| D336,517 S | 6/1993 | McKeown |
| 5,217,372 A | 6/1993 | Truocchio |
| 5,231,973 A | 8/1993 | Dlckie |
| 5,263,606 A | 11/1993 | Dutt |
| 5,308,242 A | 5/1994 | McLaughlin et al. |
| 5,334,013 A | 8/1994 | Meller |
| 5,348,473 A | 9/1994 | Kivlighan, Jr. |
| 5,352,118 A | 10/1994 | Franetzki et al. |
| 5,352,119 A | 10/1994 | Sakurai |
| 5,374,189 A | 12/1994 | Mendoza |
| D355,971 S | 2/1995 | Meller |
| D356,866 S | 3/1995 | Meller |
| D370,063 S | 5/1996 | Spreckelmeier |
| 5,538,425 A | 7/1996 | Reeves |
| D373,636 S | 9/1996 | Martin |
| 5,562,446 A | 10/1996 | Matsui et al. |
| D378,235 S | 2/1997 | Mark |
| D378,412 S | 3/1997 | Badoz et al. |
| 5,674,068 A | 10/1997 | Eibofner |
| 5,681,409 A | 10/1997 | Lin et al. |
| 5,692,901 A * | 12/1997 | Roth et al. .................. 433/85 |
| D389,912 S | 1/1998 | Emerson et al. |
| 5,733,120 A | 3/1998 | Yao et al. |
| 5,772,436 A | 6/1998 | Matsui et al. |
| 5,782,634 A | 7/1998 | Lingenhole et al. |
| 5,797,743 A | 8/1998 | Bailey |
| 5,807,108 A | 9/1998 | Schwenoha et al. |
| 5,810,588 A | 9/1998 | Cohen |
| 5,902,108 A | 5/1999 | Nakayama et al. |
| 5,911,577 A | 6/1999 | Henrikson |
| 5,921,777 A | 7/1999 | Dorman |
| 5,924,206 A | 7/1999 | Cote et al. |
| 5,924,865 A | 7/1999 | Quinn |
| 5,984,654 A | 11/1999 | Mendoza et al. |
| D425,988 S | 5/2000 | Frank |
| D426,636 S | 6/2000 | Herring |
| D427,311 S | 6/2000 | Henrikson |
| D427,682 S | 7/2000 | Novak |
| D428,652 S | 7/2000 | Frezel et al. |
| 6,099,309 A | 8/2000 | Cardarelli |
| 6,149,430 A | 11/2000 | Nemetz et al. |
| 6,186,784 B1 | 2/2001 | Bailey |
| D440,817 S | 4/2001 | Armando et al. |
| 6,305,935 B1 | 10/2001 | Cardarelli |
| 6,315,560 B1 | 11/2001 | Krouglicof et al. |
| 6,350,124 B1 | 2/2002 | Wade |
| D463,556 S | 9/2002 | Bareth et al. |
| D465,279 S | 11/2002 | Etter et al. |
| D472,969 S | 4/2003 | Wilden |
| 6,579,093 B2 | 6/2003 | Bailey et al. |
| 6,638,068 B2 | 10/2003 | Lingenhole et al. |
| 6,676,374 B2 | 1/2004 | Hashimoto et al. |
| D489,134 S | 4/2004 | Nakanishi |
| 6,716,028 B2 | 4/2004 | Rahman et al. |
| D495,799 S | 9/2004 | Hirsch et al. |
| 6,821,119 B2 | 11/2004 | Shortt et al. |
| D499,486 S | 12/2004 | Kuhn et al. |
| D504,949 S | 5/2005 | Kuhn et al. |
| D513,927 S | 1/2006 | Chen |
| 7,008,224 B1 | 3/2006 | Browning et al. |
| D520,138 S | 5/2006 | Kuhn et al. |
| D532,907 S | 11/2006 | Feinbloom et al. |
| D533,276 S | 12/2006 | Nakanishi |
| D533,946 S | 12/2006 | Lintner et al. |
| 7,214,060 B2 | 5/2007 | Maitre |
| D548,342 S | 8/2007 | Cohen |
| D550,358 S | 9/2007 | Nakanishi |
| D555,972 S | 11/2007 | Rae |
| D556,323 S | 11/2007 | Nakanishi |
| D572,822 S | 7/2008 | Thomssen et al. |
| D577,824 S | 9/2008 | Thomssen et al. |
| D579,565 S | 10/2008 | Thomssen et al. |
| D579,566 S | 10/2008 | Thomssen et al. |
| D580,054 S | 11/2008 | Thomssen et al. |
| D580,055 S | 11/2008 | Thomssen et al. |
| D580,550 S | 11/2008 | Thomssen et al. |
| D584,411 S | 1/2009 | Thomssen et al. |
| D588,698 S | 3/2009 | Thomssen et al. |
| D592,308 S | 5/2009 | Thomssen et al. |
| 2002/0119420 A1 | 8/2002 | Bailey et al. |
| 2006/0121413 A1 | 6/2006 | Turner |
| 2006/0183073 A1 | 8/2006 | Browning et al. |
| 2006/0183074 A1 | 8/2006 | Brennan |

FOREIGN PATENT DOCUMENTS

| | | |
|---|---|---|
| EP | 0925762 A1 | 6/1999 |
| GB | 1023481 | 5/1985 |
| GB | 2071913 | 5/1998 |
| JP | H1-145056 | 6/1989 |
| JP | 1211559 | 8/1989 |
| JP | H9-70407 | 3/1997 |
| JP | 2000-508951 | 7/2000 |
| WO | WO 91/15160 | 10/1991 |
| WO | WO 95/12361 | 5/1995 |
| WO | WO 96-12444 | 5/1996 |
| WO | WO 97/40768 | 11/1997 |
| WO | WO 02/076308 A2 | 10/2002 |
| WO | WO 2004-082501 A2 | 9/2004 |

OTHER PUBLICATIONS

Dental EZ Group Star Dental Solara Series Brochure in 6 pages, 2003 Dental EZ Group, Malvem, PA.

Dental EZ Group StarDental 430 Series LubeFree High-Speed Handpiece System Brochure in 4 pages, 2005 Dental EZ Group, Lancaster, PA.

DENTSPLY Professional Midwest Stylus Brochure in 2 pages, 2005 DENTSPLY International, Des Plaines, IL.

DENTSPLY Professional Midwest System Brochure in 8 pages, 2002 DENTSPLY International, Des Plaines, IL.

International Search Report for International Application No. PCT/US2008/074667, dated Nov. 10, 2008, in 2 pages.

Office Action dated Jul. 20, 2007 for Japanese Design Application No. 2007-7115.

Preliminary Report on Patentability for International Application No. PCT/US2008/074667, dated Mar. 2, 2010, in 9 pages.

Written Opinion of the International Search Report Authority for Application No. PCT/US2008/074667, dated Nov. 10, 2008 in 9 pages.

* cited by examiner

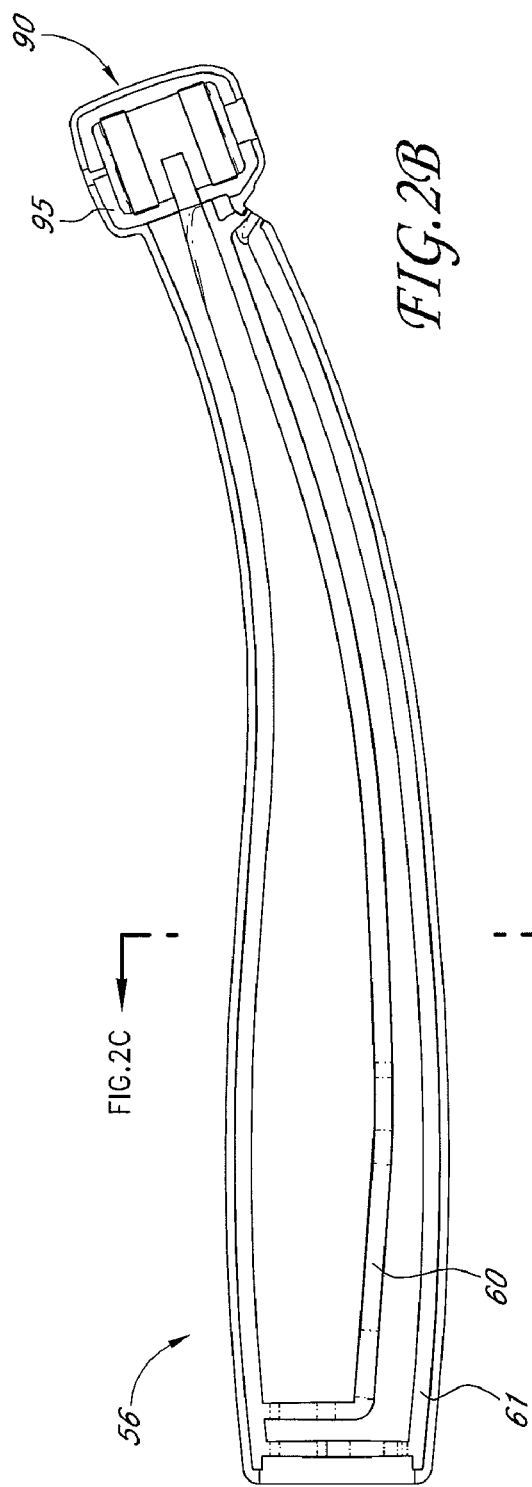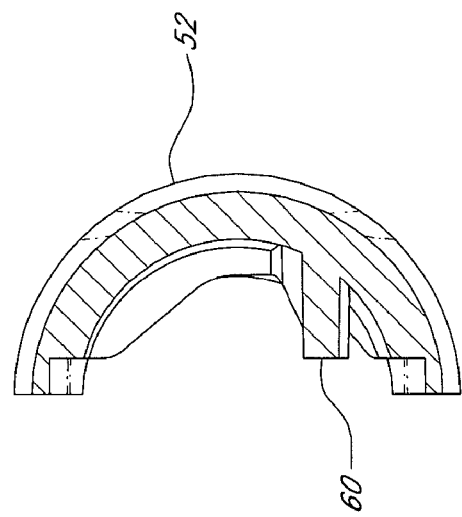

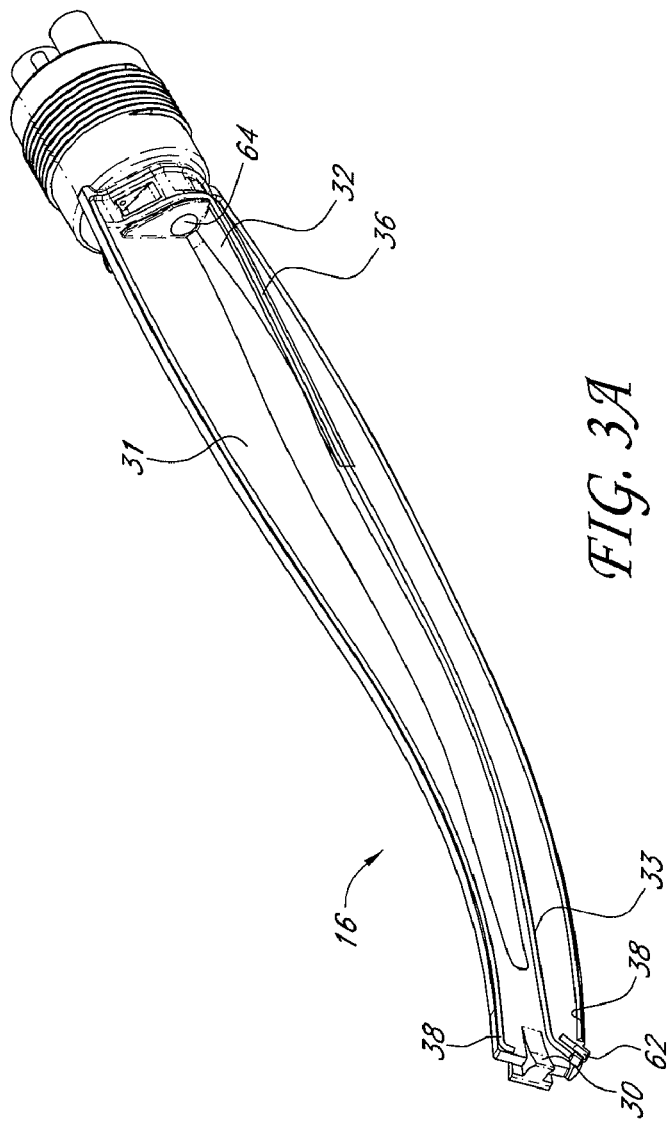
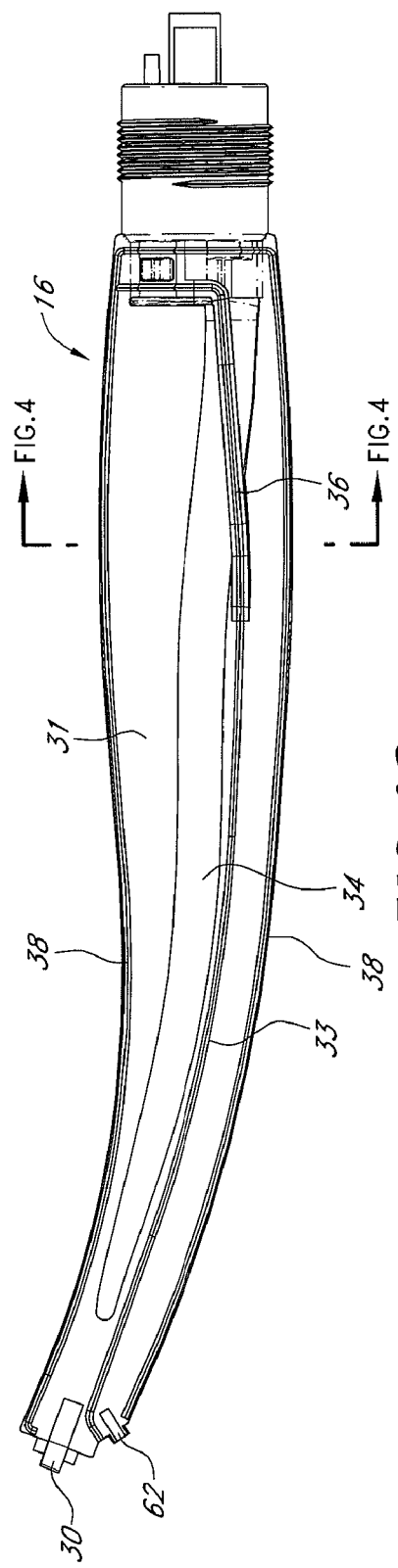
FIG. 3A
FIG. 3B

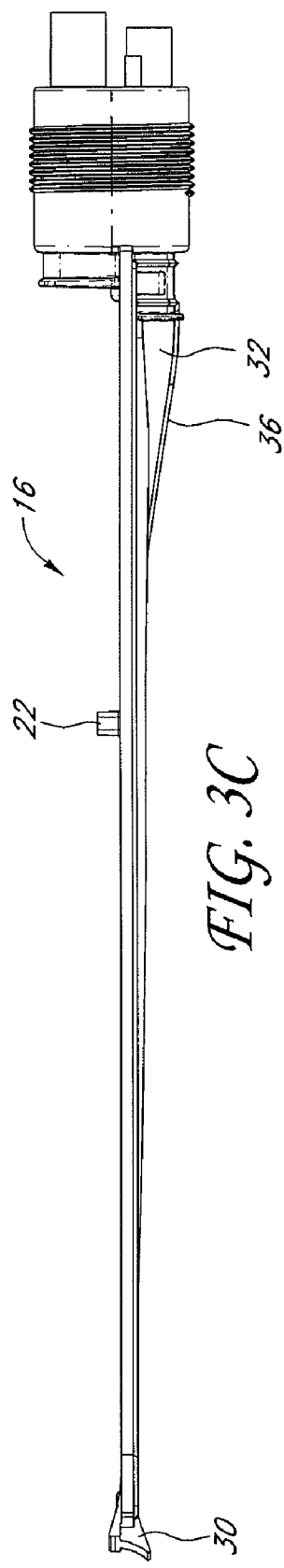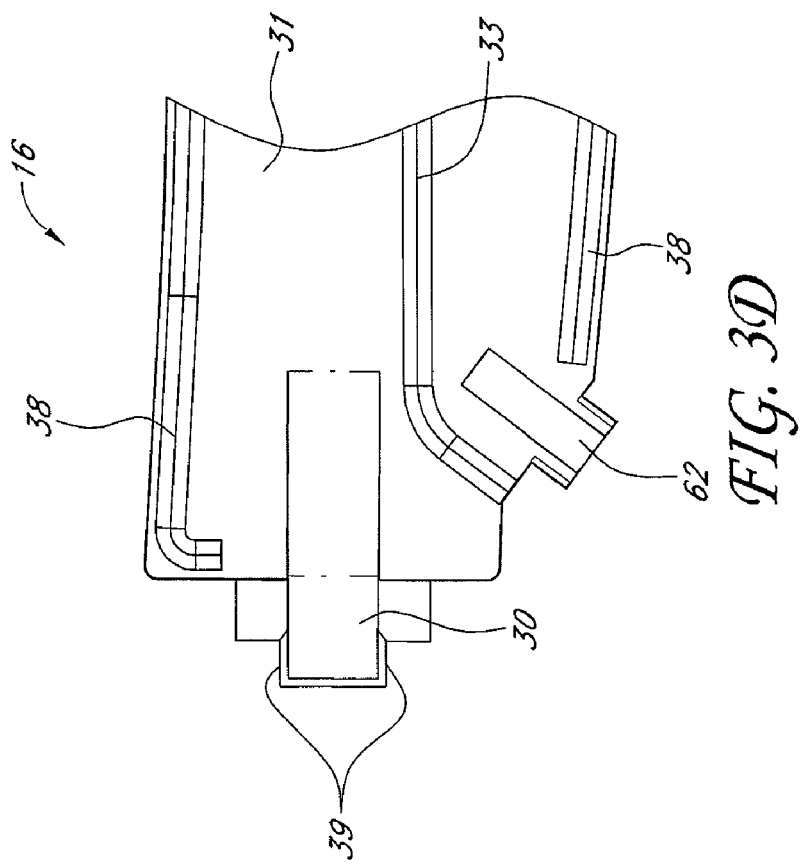
FIG. 3C
FIG. 3D

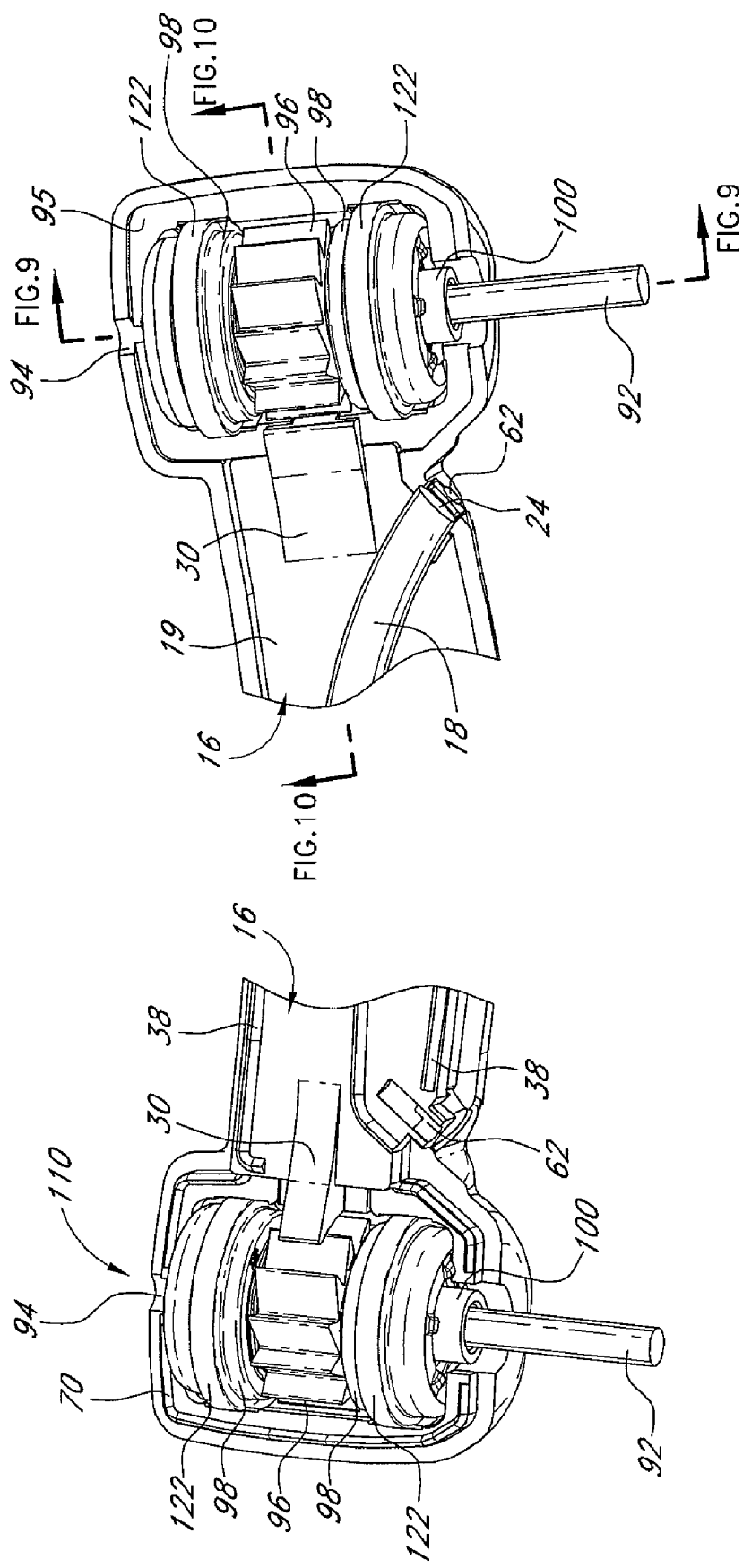

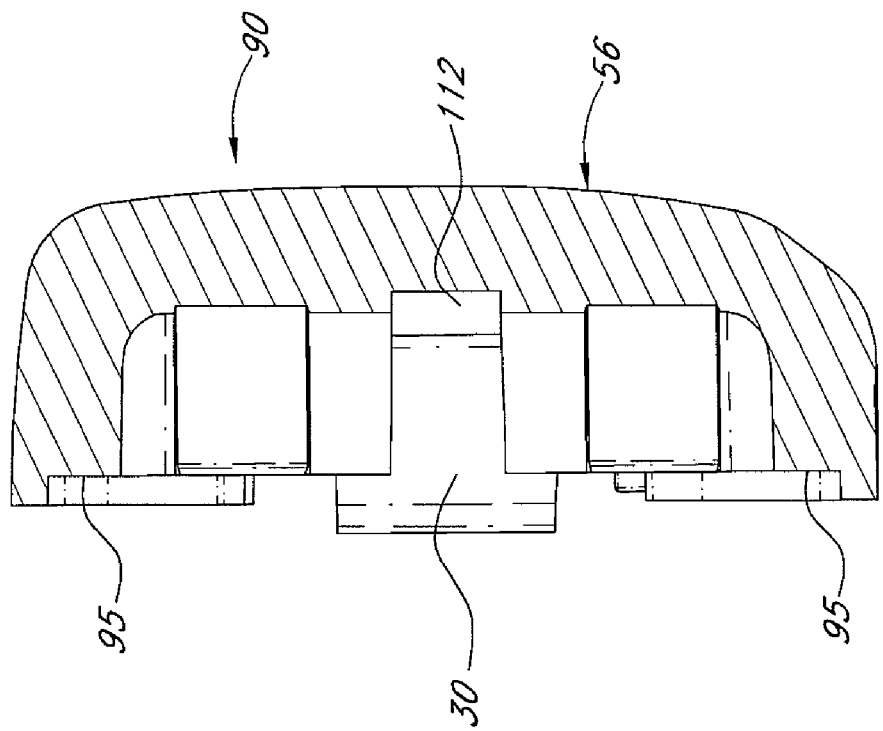
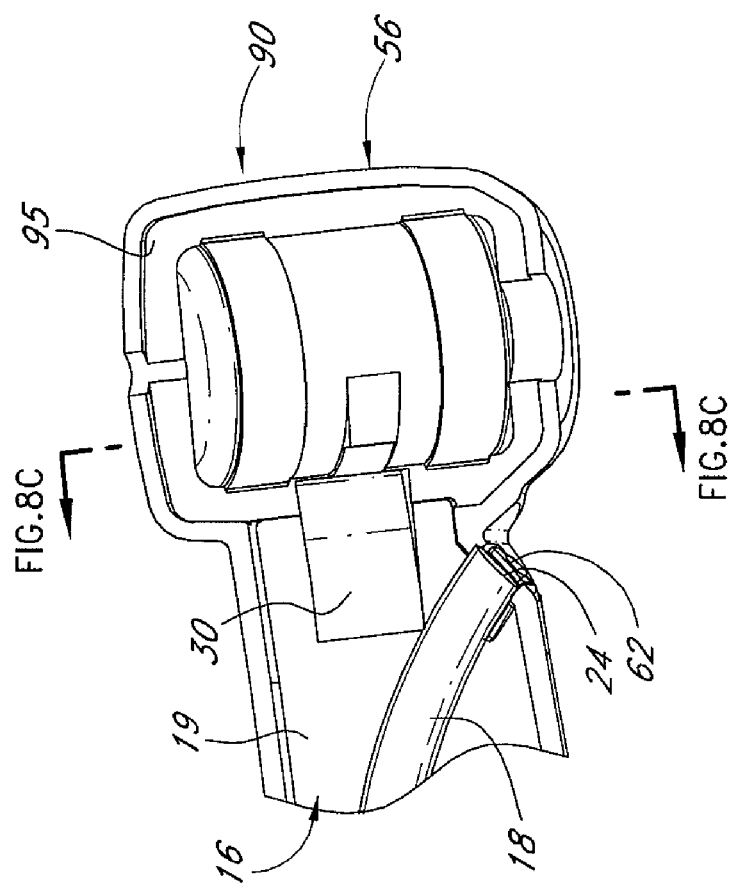

DISPOSABLE DENTAL HANDPIECE

This application is a non-provisional of and claims benefit under 35 U.S.C. §119(e) to U.S. Provisional Patent Application No. 60/969,094, filed Aug. 30, 2007, which is incorporated in its entirety by reference herein.

BACKGROUND OF THE INVENTION

1. Field of the Invention

The present invention relates generally to a handpiece for dental procedures, and more particularly to a disposable hand-held instrument for dental drilling.

2. Background

Common dental procedures involve the use of a drill to reduce at least a portion of a tooth prior to performing work on the area of the mouth on or near the tooth. In some instances, decayed enamel is removed from a tooth prior to replacement with a hardened substitute. In some instances, some or all of a tooth is removed with a dental drill prior to work beneath the gum line.

Typical drills used for such work have several components. First, a handpiece, typically constructed from stainless steel, or a steel alloy is used. An appropriate bit is selected for the work to be accomplished. Some bits have variable lengths and surface properties which affect the character of operation. The bit is then inserted into a rotating portion of the handpiece, and securely coupled to it. Finally, a source of pressurized air is connected to the handpiece, the flow of which is directed within the handpiece to rotate the turbine, which in turn rotates the bit at speeds useful for drilling.

After the handpiece has been used to perform a procedure on a patient, the handpiece is typically flushed with air or water for approximately 20 to 30 seconds in an attempt to discharge material that might have entered the turbine and/or air and water channels. The handpiece is then disconnected from the air source, and the bit is removed. Previously, the bit and handpiece have been sterilized, usually by steam or chemicals in an autoclave, requiring time between procedures or, in a busy office, the purchase of multiple handpieces and bits to allow for continuous use during sterilization.

The cost of the handpieces individually can be high. Moreover, the cost to refurbish reusable handpieces when the performance of certain features, such as bearings or light sources, degrades can be high. Additionally, handpieces may not be completely sterilized after use, or sterilized handpieces may not be properly sterilized or maintained in a sterile container after cleaning prior to use on a subsequent patient, increasing the exposure to potentially unclean environments. Although some disposable handpieces exist, they are often not provided in a sterile package and typically have inferior performance characteristics to reusable handpieces. Thus, the need exists for a sufficiently powerful, low-cost handpiece which can be assured of sterility for use on a single patient.

SUMMARY OF THE INVENTION

An aspect of at least one of the embodiments disclosed herein includes the realization that dental handpieces can be run with air, and that incorporating a structure which delivers air to the turbine blades of the handpiece in an efficient and high speed manner is advantageous.

Thus, in accordance with an embodiment, a disposable dental instrument driven by compressed air comprises an elongated body comprising a first shell half, a second shell half, and a core, the shell halves joined to form an exterior surface for manual manipulation, the shell halves additionally forming a cavity, the cavity having various passageways as fluid conduits. The dental instrument further comprises a base comprising a plurality of conduits, the base communicating with an outside source of light and fluid through the conduits, the conduits communicating with the passageways defined by the elongated body, and a head located at the opposite end from the base, the head comprising a turbine shaft rotatably mounted within the head. The dental instrument further comprises a turbine impeller, the turbine impeller connected to the turbine shaft, the turbine impeller being driven by an outside source of air through an air nozzle to rotate a dental bit, at least one opening located under the head configured to deliver fluid away from the dental instrument, at least one opening located under the head configured to deliver light away from the dental instrument, and wherein the air nozzle has a rectangular cross-sectional shape to create an airflow which more closely matches a rectangular cross section of a turbine blade.

Another aspect of at least one of the embodiments disclosed herein includes the realization that sealing two shell halves and a core together to form various conduits or passageways for light, air, and/or water can be difficult, and can lead to imperfections in the assembly. Including tapered mating portions on the core and left shell half can provide a gradually changing distance from the surface of the core for welding, thereby reducing or eliminating shape changes sufficiently sharp to cause imperfections in a sonic welding assembly.

Thus, in accordance with an embodiment, a disposable dental instrument driven by compressed air comprises an elongated body comprising a first shell half, a second shell half, and a core, the shell halves joined to form an exterior surface for manual manipulation, the shell halves additionally forming a cavity, the cavity having various passageways as fluid conduits. The dental instrument further comprises a base comprising a plurality of conduits, the base communicating with an outside source of light and fluid through the conduits, the conduits communicating with the passageways defined by the elongated body. The dental instrument further comprises a head located at the opposite end from the base, the head comprising a turbine shaft rotatably mounted within the head, a turbine impeller, the turbine impeller connected to the turbine shaft, the turbine impeller being driven by an outside source of air through an air nozzle to rotate a dental bit. The dental instrument comprises at least one opening located under the head configured to deliver fluid away from the dental instrument, and at least one opening located under the head configured to deliver light away from the dental instrument. The core comprises a flange extending away from a central face of the core, and a seam disposed along the edge of the flange, and wherein the first shell half comprises a wall extending towards the central face of the core, the wall having a tapered portion, the tapered portion being sized and shaped to mate with the flange.

Another aspect of at least one of the embodiments disclosed herein includes the realization that it is advantageous for dental instruments to direct light to a patient's tooth or interaction region, so as to better view what work is being done. Thus, it is desirable to have a reliable, stable light source attached to and within the dental handpiece to deliver light from the handpiece.

Thus, in accordance with an embodiment, a disposable dental instrument driven by compressed air comprises an elongated body comprising a first shell half, a second shell half, and a core, the shell halves joined to form an exterior surface for manual manipulation, the shell halves additionally forming a cavity, the cavity having various passageways as fluid conduits. The dental instrument further comprises a base comprising a plurality of conduits, the base communicating with an outside source of light and fluid through the conduits, the conduits communicating with the passageways defined by the elongated body. The dental instrument further comprises a head located at the opposite end from the base, the head comprising a turbine shaft rotatably mounted within the head, a turbine impeller, the turbine impeller connected to the turbine shaft, the turbine impeller being driven by an outside source of air through an air nozzle to rotate a dental bit. The dental instrument further comprises at least one opening located under the head configured to deliver fluid away from the dental instrument, and at least one opening located under the head configured to deliver light away from the dental instrument. The dental instrument further comprises a light rod configured to deliver light to one of the openings, the light rod comprising a tab extending from a body of the light rod, wherein the center core comprises at least one molded projection configured to engage the light rod tab and inhibit motion of the light rod in at least one direction.

Another aspect of at least one of the embodiments disclosed herein includes the realization that directing air to a turbine within the dental instrument can be made more efficient through the use of a flow deflector. The geometry of the flow deflector can increase air speed, reduce noise, and direct the air flow in a particular manner within the turbine area of the handpiece.

Thus, in accordance with an embodiment, a disposable dental instrument driven by compressed air comprises an elongated body comprising a first shell half, a second shell half, and a core, the shell halves joined to form an exterior surface for manual manipulation, the shell halves additionally forming a cavity, the cavity having various passageways as fluid conduits. The dental instrument further comprises a base comprising a plurality of conduits, the base communicating with an outside source of light and fluid through the conduits, the conduits communicating with the passageways defined by the elongated body. The dental instrument further comprises a head located at the opposite end from the base, the head comprising a turbine shaft rotatably mounted within the head, a turbine impeller, the turbine impeller connected to the turbine shaft, the turbine impeller being driven by an outside source of air through an air nozzle to rotate a dental bit. The dental instrument further comprises at least one opening located under the head configured to deliver fluid away from the dental instrument, and at least one opening located under the head configured to deliver light away from the dental instrument. The core further comprises a flow deflector located on the end of the core nearest the head, the flow deflector projecting further towards the first shell half than towards the second shell half, an edge of the flow deflector forming a part of the air nozzle.

Another aspect of at least one of the embodiments disclosed herein includes the realization that reducing the weight of a dental handpiece can save on cost, as well as make the handpiece easier to ship and use.

Thus, in accordance with an embodiment, a disposable dental instrument driven by compressed air comprises an elongated body comprising a first shell half, a second shell half, and a core, the shell halves joined to form an exterior surface for manual manipulation, the shell halves additionally forming a cavity, the cavity having various passageways as fluid conduits. The dental instrument further comprises a base comprising a plurality of conduits, the base communicating with an outside source of light and fluid through the conduits, the conduits communicating with the passageways defined by the elongated body. The dental instrument further comprises a head located at the opposite end from the base, the head comprising a turbine shaft rotatably mounted within the head, a turbine impeller, the turbine impeller connected to the turbine shaft, the turbine impeller being driven by an outside source of air through an air nozzle to rotate a dental bit. The dental instrument further comprises at least one opening located under the head configured to deliver fluid away from the dental instrument, and at least one opening located under the head configured to deliver light away from the dental instrument. The turbine shaft further comprises blades, the turbine shaft having cavities formed within the outer boundary of the blades.

BRIEF DESCRIPTION OF THE DRAWINGS

These and other features and advantages of the present embodiments will become more apparent upon reading the following detailed description and with reference to the accompanying drawings of the embodiments, in which:

FIG. 2B is a right side elevational view of an embodiment of a left shell component of a dental instrument.

FIG. 2C is a cross-sectional view of the embodiment of FIG. 2B.

FIG. 3A is a front, top, and left side perspective view of an embodiment of a center core of a dental instrument.

FIG. 3B is a left side perspective view of an embodiment of a center core of a dental instrument.

FIG. 3C is a top plan view of an embodiment of a center core of a dental instrument.

FIG. 3D is a partial left side perspective view of an embodiment of a center core of a dental instrument.

FIG. 7 is a partial left side elevational view of an embodiment of a dental instrument, with the left shell half removed.

FIG. 8A is partial right side elevational view of an embodiment of a dental instrument with the right shell half removed.

FIG. 8B is a partial right side elevational view of an embodiment of a dental instrument with the right shell half and impeller assembly removed.

FIG. 8C is a cross sectional view of the embodiment of FIG. 8B.

DETAILED DESCRIPTION OF THE PREFERRED EMBODIMENT

Figure 1A:
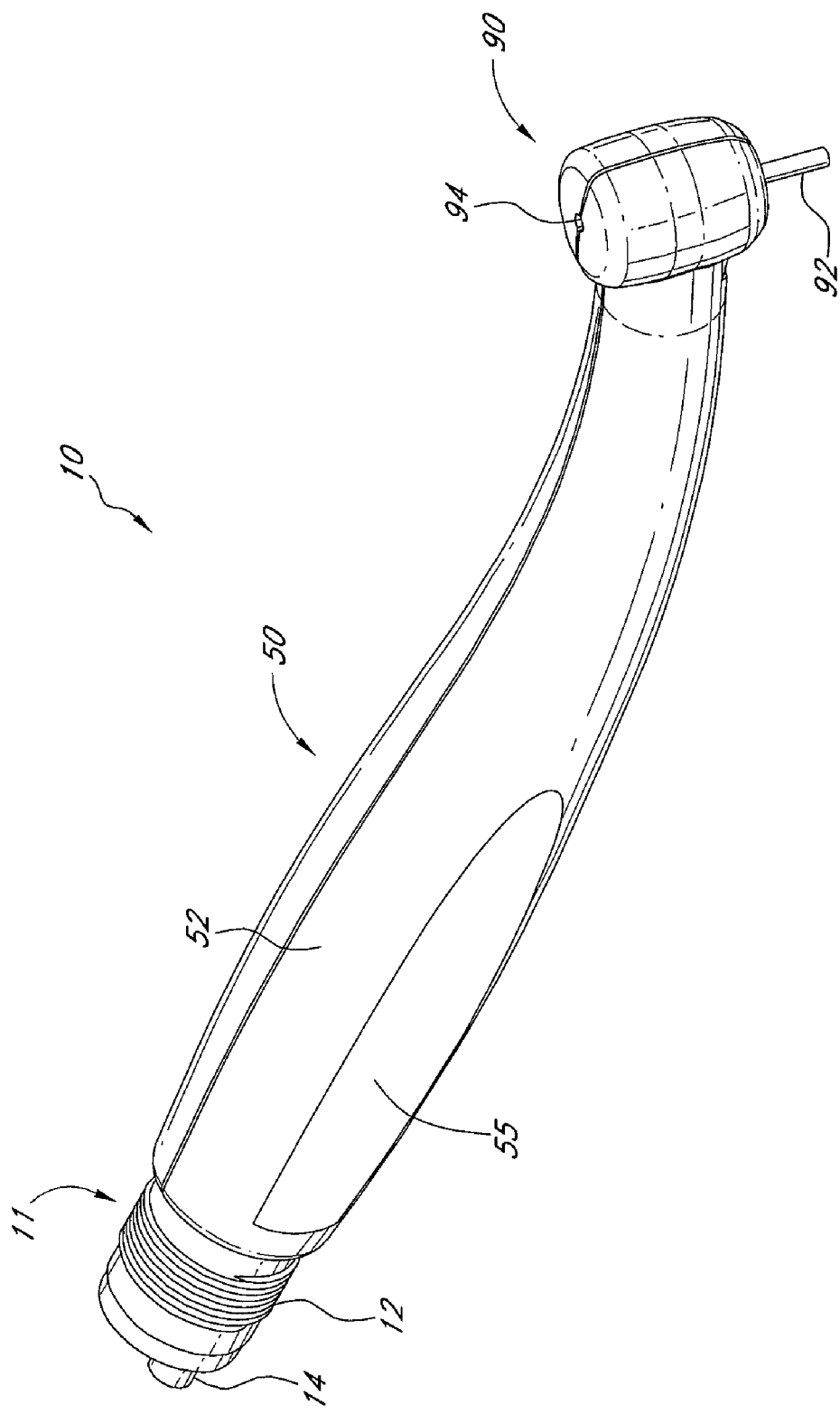
FIG. 1A is a front, top, and right side perspective view of an embodiment of a dental instrument.

With reference to FIG. 1A, an embodiment of the handpiece 10 generally includes a base 11, body 50, and head 90. The handpiece 10 is advantageously sized to fit comfortably in the human hand. The handpiece 10 can be connected to a source of various fluids under pressure, including but not limited to air and water. A light source can also be connected to the handpiece 10. Light from the light source can be directed by means of a light pipe to illuminate an interaction region on or near a patient's tooth. During operation, an operator controllably introduces pressurized air into a first portion of the handpiece 10, shaped to direct the air to a turbine in the head 90. The turbine, having both impeller blades and a shaft coupled to a drill bit, is turned by the pressurized air, causing the drill bit to rotate at high speeds. Preferably, the drill speeds are useful for dental procedures. By controlling the supply of pressurized air to the handpiece 10, the speed of the drill can be altered by the operator. The pressurized air can leave the head and exit by passing through a second portion of the handpiece 10, the second portion connected to an exhaust conduit. Pressurized air and/or cooling water can also be provided to a third portion of the handpiece, which is directed to exit near the head for clearing debris from the interaction area of the drill bit. In some embodiments, pressurized water is used instead of air in the third portion.

Figure 1B:
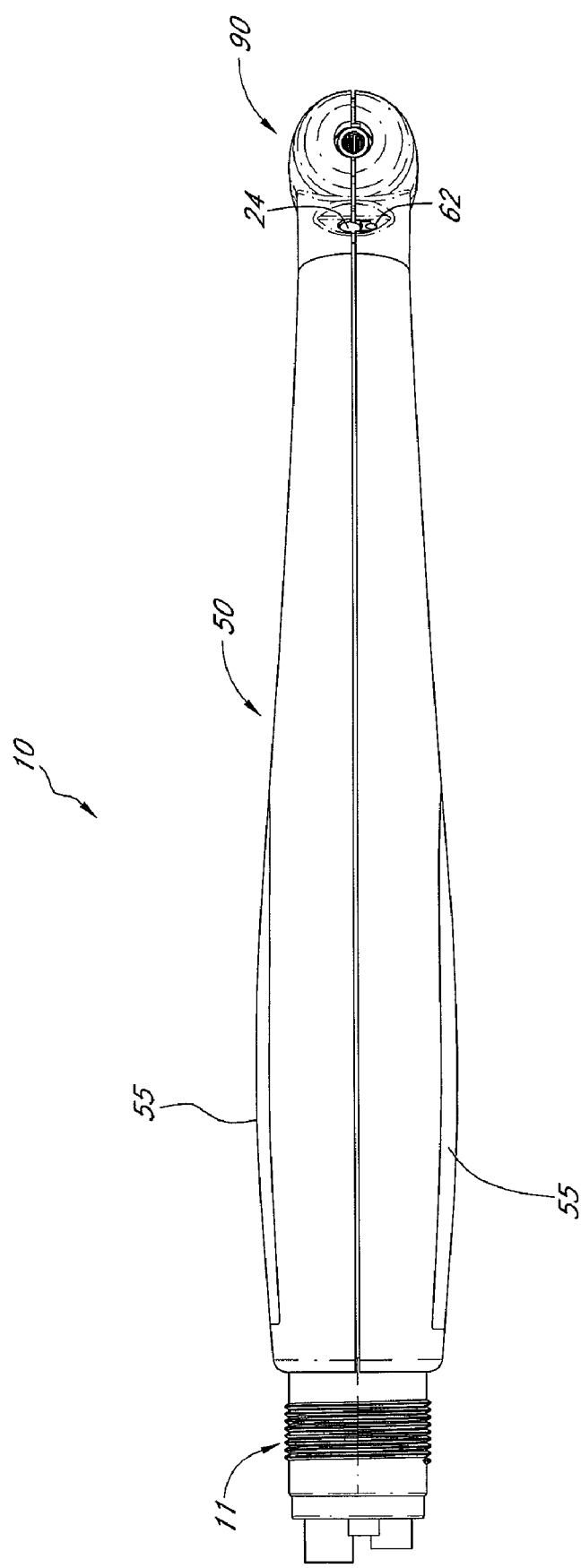
FIG. 1B is a bottom plan view of an embodiment of a dental instrument.

With reference to FIGS. 1A and 1B, the base 11 has a generally cylindrical shape. Other shapes are also possible. External threads 12 are adapted to couple the base 11 to a fluid source (not shown). Base 11 can be manually engaged and disengaged without the use of additional tools. A plurality of conduits 14 in base 11 permit passage of fluids from their source to the interior of the handpiece 10. The number and size of conduits 14 can correspond to any standard fluid source used with dental instruments.

With continued reference to FIGS. 1A and 1B, the body portion 50 has an exterior surface 52. The surface 52 can be formed with various textures or materials to aid gripping by the operator. These can include, among others, indentations or protrusions, a rough surface, and/or the addition of ribbed or rubberized members. For example, and with reference to FIGS. 1A and 1B, the body 50 can include a molded insert portion or portions 55. The molded insert portion 55 can be used as a location for a rubberized member. The rubberized member can add to the aesthetic appearance of the body 50, and can also aid in gripping the dental instrument.

Figure 6:
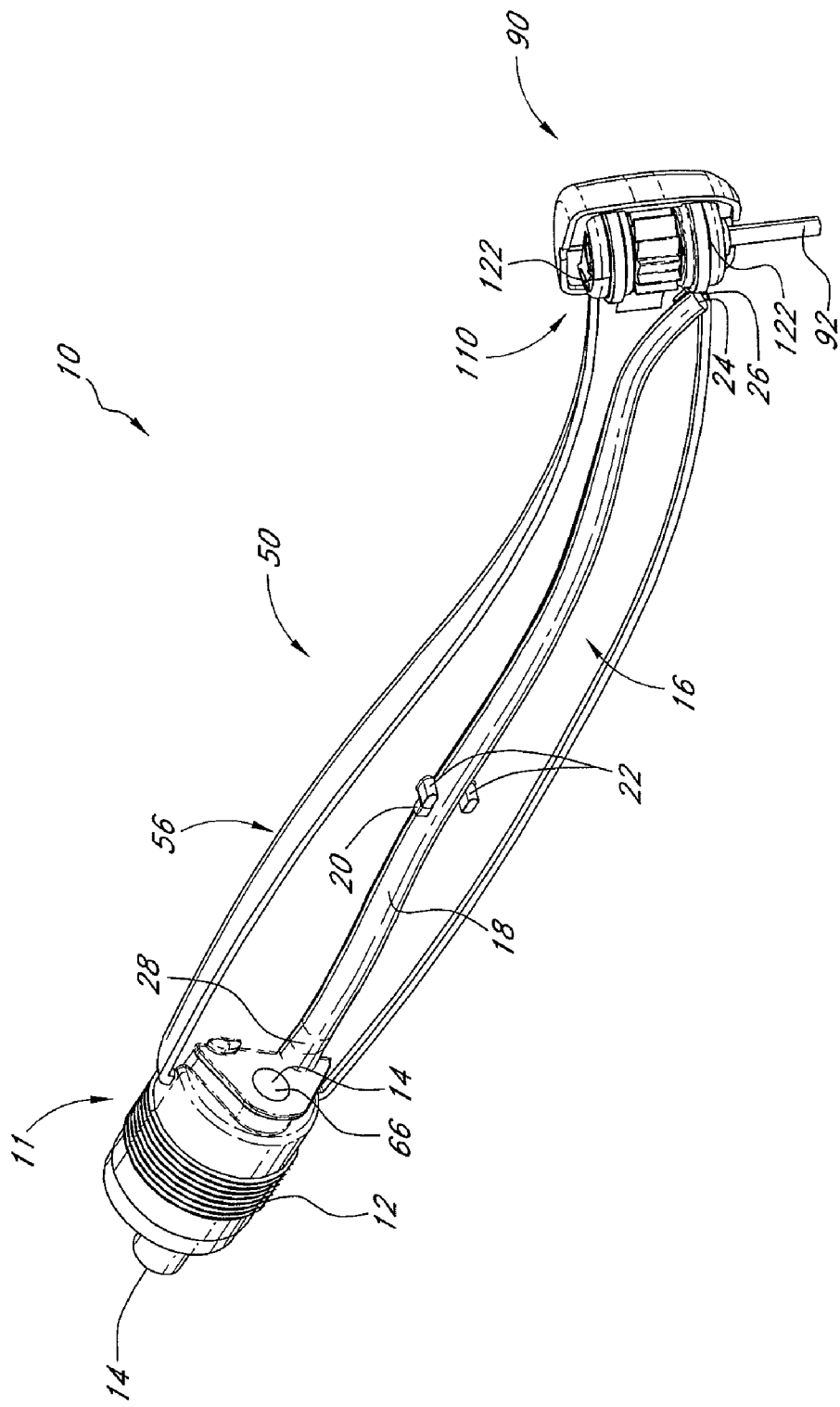
FIG. 6 is a front, top, and right side perspective view of an embodiment of a dental instrument, with the right shell half removed.

With reference to FIGS. 1A, 1B, and 6, the head 90 has a generally cylindrical shape enclosing an impeller assembly 110, and is adapted to receive, engage, and rotate a drill bit 92. In some embodiments, a circular bit 92 can be received by a non-circular shaped receiving portion. For example, in some embodiments, an hexagonal-shaped receiving portion, or chuck, can be used in the head 90. It has been found that using a hexagonal-shaped receiving portion with a circular bit 92 can advantageously help reduce noise and vibration. Other shapes and configurations are also possible.

The head 90 is integrally formed with the body 50, as shown. In some embodiments the head 90 generally retains an air flow within its interior and inhibits air leakage to the ambient environment, thereby helping to minimize power loss and reduce noise levels.

Figure 2A:
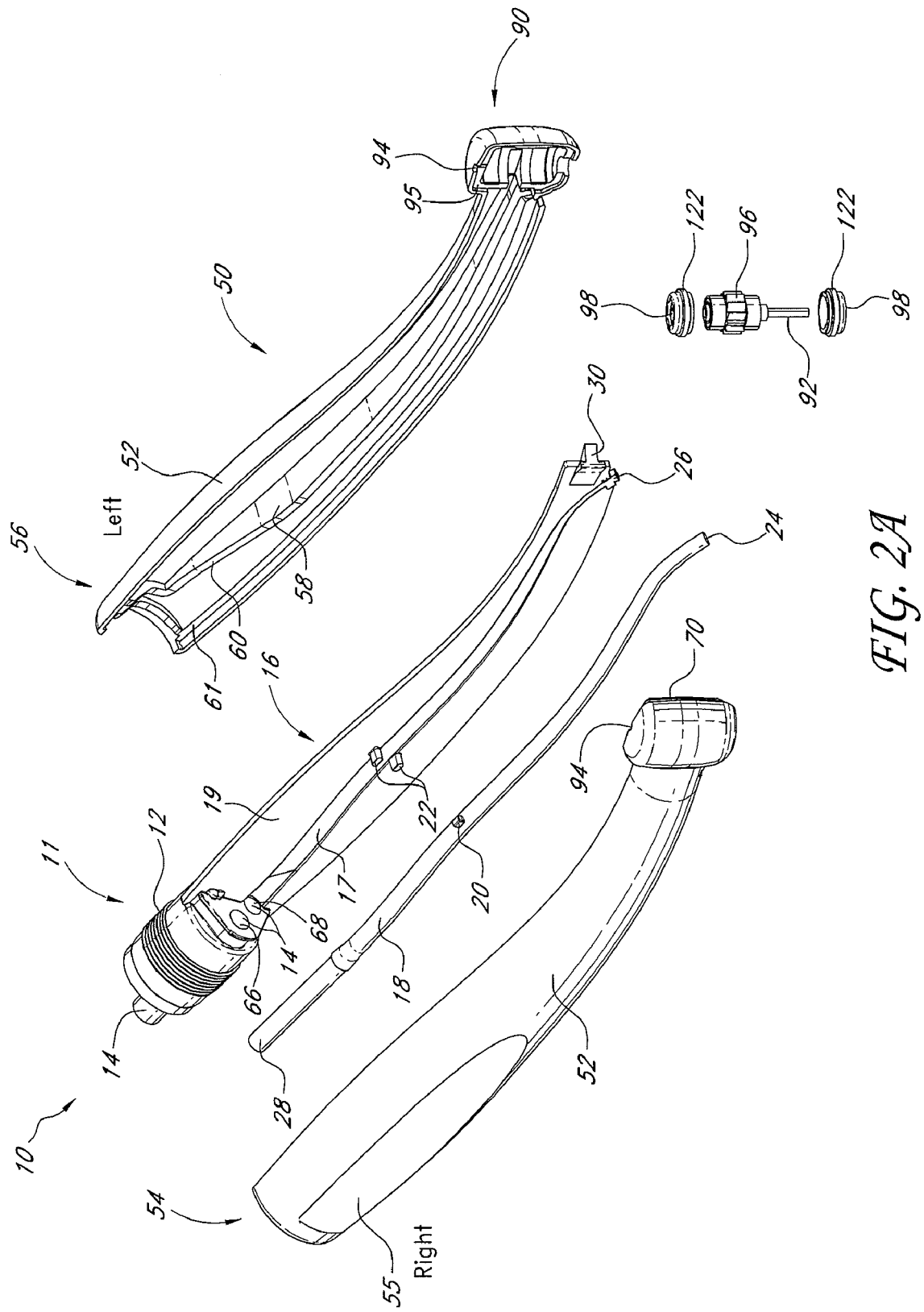
FIG. 2A is an exploded perspective view of an embodiment of a dental instrument.

With reference to FIGS. 2A-C, the handpiece 10 is constructed from several individual components. In the illustrated embodiment, a right shell 54 and a left shell 56 can be joined around a center core 16 to form the body 50. In some embodiments, the left shell 56 can include a protruding wall portion 58 which has a tapered portion 60 as shown in FIGS. 2B and 2C.

With continued reference to FIGS. 2A-C, the center core 16 is integrally formed with the base 11 and extends down the body 50 of the handpiece 10 toward the head 90. The center core 16 advantageously extends in a generally planar shape down the length of the body 50, and can include a generally flat face and mating area 19 along its right side for mating with the right shell 54. The core 16 can extend from the base of the handpiece 10 to the front and partition the interior of the body 50 into at least two segments. In the embodiment shown, the center core 16 inhibits fluid from passing between or around the core 16 from the side disposed toward the interior of the right shell 54 into the side disposed toward the interior of the left shell 56 and vice versa. Thus, air or another fluid pressurized to travel on one side of center core 16 is contained by the center core 16, and does not escape to the other side of the handpiece 10.

With reference to FIG. 2A, a groove 17 extends along at least part of the center core 16 along the right side. The groove 17 can be used to hold a portion or portions of a light rod 18 or other similar structure in place within the body 50.

With reference to FIGS. 3A-3D, the left side of the center core 16 has a concavity 34 where the groove 17 is accommodated on the other side of the center core 16. A seam 33 used for assembly of the handpiece 10 extends along the side of the center core 16. The seam 33 has an apex 36 in a triangular shape when viewed as a cross-section, but other shapes can also be used. Additionally, the center core 16 has a flange 32 extending outward from the face 31 of the center core 16. The seam 33 is disposed along the edge of the flange 32. Although the concavity 34 is on the left side of the center core 16 in the illustrated embodiment, and the flange 32 on the left, in some embodiments, they can be in different positions or locations.

Figure 4:
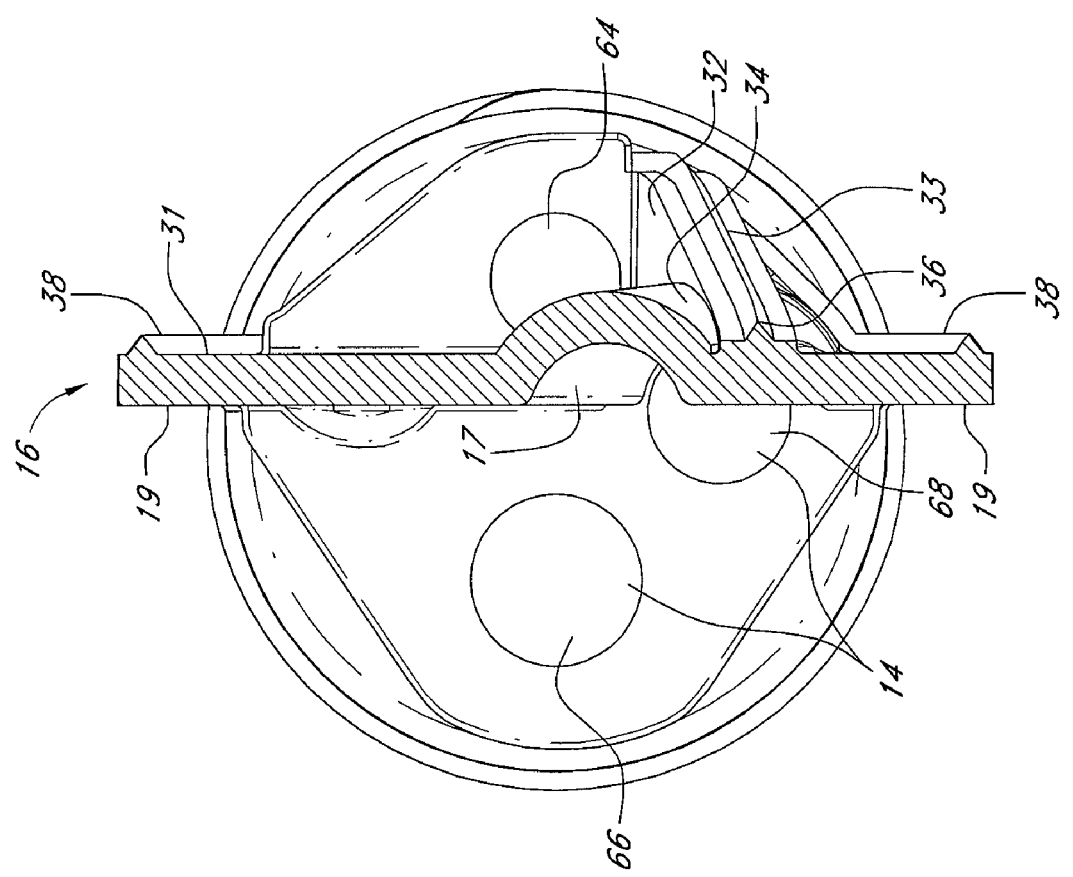
FIG. 4 is a cross sectional view of the embodiment of FIG. 3B.

With reference to FIGS. 2-4, the flange 32 has a triangular shape, tapered toward the head 90. The left shell 56 can have a correspondingly-shaped horizontal wall 58 with a taper portion 60. In at least some embodiments, the wall 58 extends generally perpendicularly in relation to the face 31 of the center core 16. The taper portion 60 of the wall 58 can be sized and shaped to complement the flange 32, thereby completing the wall 58, and filling in the missing section of the taper portion 60. In some embodiments, the wall 58 can be a location for sonic welding, such as ultrasonic welding, to join the left shell 56 to the center core 16 along the seam 33. In some embodiments the taper portion 60 can have an indented cross-section to receive the apex 36 along the outer edge of the seam 33. The peak and receptive shape can aid in securing the portions during sonic welding. Other shapes and configurations are also possible. The taper 60 also provides a gradually changing distance from the surface 31 of the center core 16, thereby reducing or eliminating shape changes sufficiently sharp to cause imperfections in a sonic welding assembly.

With reference to FIGS. 2-5, the center core 16 can include additional seams or protrusions 38 along joining edges of the surface 31. The protrusions 38 have triangular-shaped cross-sections, similar to seam 33. In some embodiments the protrusions 38 can have a height between 0.015"-0.019." Other ranges are also possible, as are other shapes and configurations for the protrusions. The protrusions 38 extend along the entire joining edge of the surface 31.

With continued reference to FIGS. 2A and 2B, the left shell 56 includes flat mating surfaces 61 along its joining edge. The mating surfaces 61 are in the form of recessed areas along the edge of the left shell 56. In other embodiments, the flat mating surfaces can be in different locations, and/or not be recessed from the edge of the left shell 56. When the handpiece 10 is assembled, for example by sonic welding, the protrusions 38 mate with the mating surfaces 61, and the seam 33 mates with the wall 58 in order to join the core 16 with the left shell 56.

With continued reference to FIG. 2-5, the seam 33 and protrusions 38 substantially surround at least some of the air, water, and light openings near the head 90, helping to isolate these conduits and openings, and prevent unwanted leakage of air and/or water within the handpiece 10.

With reference to FIGS. 2A, 5, 7, and 8A the right shell 54 also includes protrusions 70, located along joining edges of the right shell 54. The protrusions 70 have triangular-shaped cross-sections, similar to seam 33 and protrusions 38. In some embodiments the protrusions 70 can have a height between 0.015"-0.019." Other ranges are also possible, as are other shapes and configurations. The protrusions 70 extend along the entire joining edge of the right shell 54. With continued reference to FIG. 2A, the core 16 includes a flat face and mating area 19, as described above. Additionally, and with continued reference to FIG. 8, the left shell 56 includes flat mating surfaces 95 along the joining edge of the head portion of the shell. When the handpiece 10 is assembled, for example by sonic welding, the protrusions 70 on the right shell 54 can melt, due to high frequencies, and mate with the mating surfaces 19 and 95 of the core 16 and left shell 56, forming a seal. Similar to protrusions 38 and seam 33 as described above, the protrusions 70 can substantially surround at least some of the air, water, and/or light openings near the head 90, helping to isolate the conduits and openings and prevent unwanted leakage of air and/or water. Additionally, and with reference to FIG. 10, an apex 160 of the protrusion 70 can be formed to aid sonic welding in the head region when the shells 54, 56 are coupled together.

With reference to FIGS. 2A, 3A-D, 7, and 8, the center core 16 has a flow deflector 30 disposed near the head 90. The flow deflector 30 can project further on one side of the center core 16 than another, as shown, or can extend equally. With continued reference to FIG. 3D, in some embodiments the center core 16 can include protrusions 39 on both the upper and lower portions of the flow deflector 30. The protrusions 39 can have a triangular-shaped cross-sections, similar to seam 33, protrusions 38, and protrusions 70. In some embodiments, the protrusions 39 can have a height between 0.005"-0.010." Other ranges are also possible, as are other shapes and configurations. The protrusions 39 are used to mate the flow deflector 30 and core 16 with the left shell 56, and further inhibit unwanted leakage of air and/or water from one area of the handpiece 10 to another.

With reference to FIGS. 2A, 3A, 3B, and 4, at least one of the conduits 14 through the base 11 can be a fluid port. For example, a port 64 can be used to direct compressed air through a passageway between the center core 16 and left shell 56, above wall 58 of the left shell 56. Another fluid conduit can be disposed beneath the wall 58 of the left shell 56, thereby fluidly isolating it from the space above the wall 58, and the compressed air. One or more conduits 14 can extend through the base 11 and enter the left side of the body 50, where the left side of the handpiece 10 is the portion between the left side of the core 16 and the interior of the left shell 56. Similarly, one or more conduits 14 can extend through the base 11 into the right side, the right side of the handpiece 10 being the portion between the right side of the core 16 and the interior of the right shell 54. In some embodiments, a vent to the ambient atmosphere can be used in place of at least one conduit 14.

With continued reference to FIGS. 2A, 3A, 3B, and 4, in some embodiments, a conduit 14 can provide water to the space beneath the wall 58. Water, under pressure from the fluid source, can travel through the body 50 and exit through the port 62 located at the end of the handpiece under the head 90. In some embodiments, other fluids can be used. For example, pressurized air can be introduced into the body 50 beneath the wall 58, resulting in air released through the fluid port 62 instead of water. The handpiece 10 can be designed to accommodate either fluid, and therefore, be configured to couple with fluid sources that provide either.

With reference to FIGS. 2A, 3C, 4, and 6, the center core 16 can be adapted to couple with a light pipe 18. The light pipe 18 can be made from a fiber optic element, and sized to fit in at least one of the conduits 14 in the base 11. Preferably, the light pipe 18 is polished along its length to aid light transmission from end to end. In some embodiments, the light pipe 18 can be formed to engage the center core 16 with a tab 20 sized and shaped to engage at least one of a plurality of molded projections 22 of the center core 16. Accordingly, when the proximal end 28 of the light pipe 18 is positioned in one of the conduits 14, the light pipe 18 can reside in the groove 17 on one side of the center core 16. The tab 20 of the light pipe 18 can then be positioned to rest against one of the molded projections 22, inhibiting motion of the light pipe 18. The distal end 24 of the light pipe 18 can then be positioned near a light exit port 26 near the head 90 of the handpiece 10. The light exit port 26 can be angled to coincide with the tip of the protruding bit 92. Thus, when light is introduced through the base 11 into a conduit 14 accommodating the light pipe 18, the light can pass through the light pipe 18 and project on to the area being drilled. The light can be provided from an external source in any standard configuration for coupling with the handpiece 10.

Figure 5:
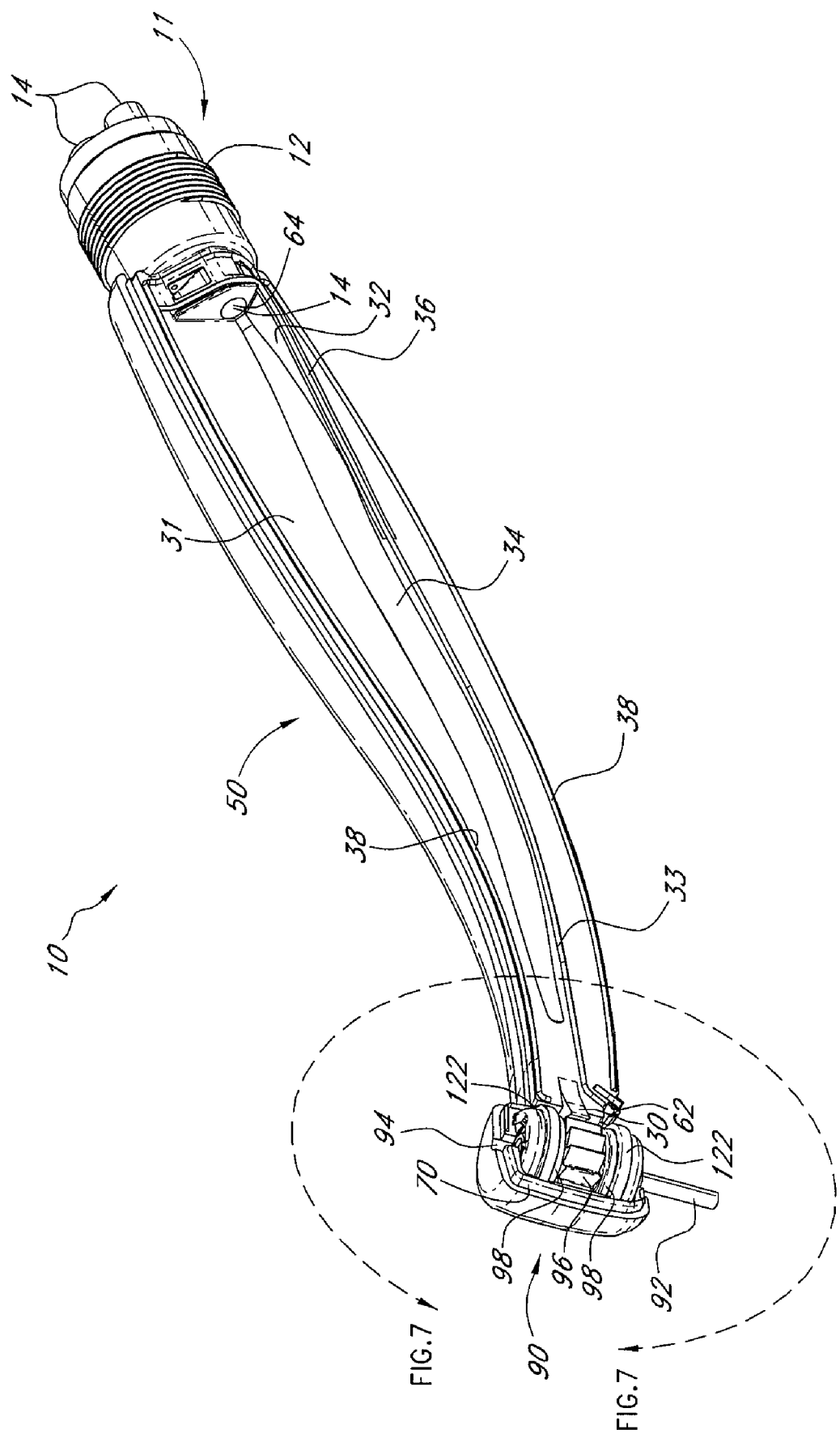
FIG. 5 is a top, front, and left side perspective view of an embodiment of a dental instrument, with the left shell half removed.

With reference to FIGS. 5 and 6, the head 90 can be formed by portions of the right 54 and left 56 shells. As shown, the shells 54, 56 can each form approximately half of the head portion 90. Thus, when joined to assemble the body portion 50, the head portion 90 is also formed, preferably containing the impeller assembly 110.

Each of the base 11 and center core 16, and the shells 54, 56 are preferably composed from the same material to reduce manufacturing costs. Some suitable materials include plastics. In some embodiments, acrylonitrile butadiene styrene (ABS) can be used. The components can be injection molded. In some embodiments, the light pipe 18 can be formed from an acrylic resin or Lucite, though other plastics and materials with fiber-optic properties can also be used. Selection of material can be made to guarantee sufficient rigidity after manufacturing. Preferably, the material chosen does not easily deform, helping keep moving parts within tolerances.

Figure 10:
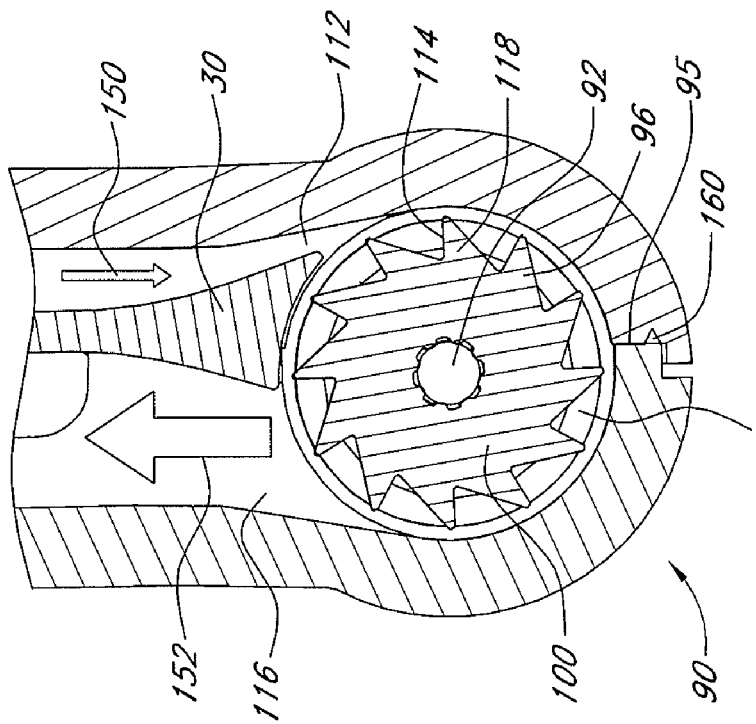
FIG. 10 is another cross-sectional view of the embodiment of FIG. 8A.
Figure 9:
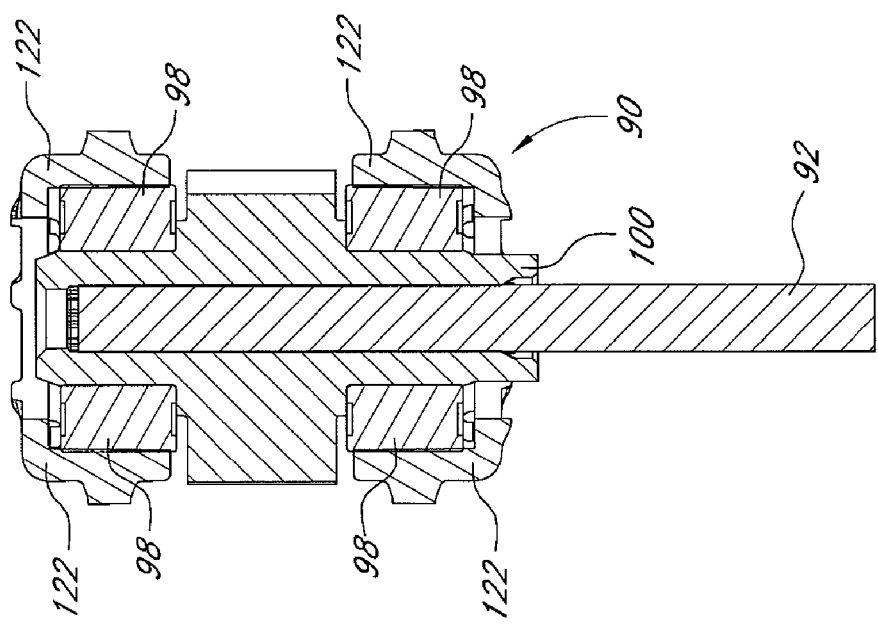
FIG. 9 is a cross-sectional view of the embodiment of FIG. 8A.

FIGS. 7-10 illustrate detailed views of the head 90 of the handpiece 10. With reference to FIG. 7, the left shell half 56 is removed to permit inspection of the impeller assembly 110. FIG. 8A illustrates an embodiment with the right shell 54 removed to permit inspection of the other side of the assembly 110. FIG. 8B illustrates an embodiment with the right shell 54 and impeller assembly both removed, leaving only the center core 16 and left shell 56. FIG. 8C illustrates a cross section of FIG. 8B. FIGS. 9 and 10 depict cross-sectional views of the head 90 taken along the axes shown in FIG. 8A.

With reference to FIGS. 7 and 8A, the impeller assembly 110 can comprise bearings surrounding and supporting an impeller shaft 100. In the illustrated embodiment, bushing bearings 98 are used, though ball bearings can also be used. The bearings 98 can be composed of plastic and are advantageously self-lubricated. In some embodiments, water or another fluid from a cavity within the body 50 can be directed onto the bearings 98 to provide lubrication.

With reference to FIGS. 7 and 8A, grommets 122 can be fitted to at least partially enclose the bearings 98. The grommets 122 can be composed of silicone rubber, though other materials, including without limitation, ethylene propylene diene monomer (EPDM) rubber, nitrile, or a thermoplastic elastomer, such as a thermoplastic vulcanizate, can also be used. The grommets 122 can have straight sides, and can have one, two, or any other number of ribs which deform once enclosed within the housing of the head 90. The grommets 122 provide a secure coupling to the head 90 for the impeller assembly 110, thereby inhibiting off-axis movement of the bit 92 during rotation. The bearings 98 can be attached to the grommets 122 by a press fit, a specific fastener, glue, or an epoxy. The grommets 122 can simplify the bearing installation, decrease noise and vibration, and provide a cushioning effect allowing the dentist to receive a feedback feeling while working. In some embodiments, the grommets are omitted, and instead a crush-rib arrangement is used. In a crush-rib arrangement, the bushing bearings 98 or ball bearings coupled to the impeller assembly 110 are inserted into the head 90 so as to plastically deform a plurality of plastic ribs within the head 90, thereby inducing an interference fit. The deformed ribs secure the bushing bearings 98 or ball bearings into position within the head 90, taking the place of the grommets 122.

With reference to FIGS. 7-12, the impeller shaft 100 can have an outward-extending portion having a plurality of impeller blades 96. The impeller blades 96 rotate around a central axis, typically corresponding to the center of the bit 92, which is supported by the bearings 98 and positioned within the shaft 100. The blades 96 preferably have a flat surface 114 and an angled portion 118. In the embodiment shown, the impeller has twelve blades equally spaced around the impeller, though more or fewer blades can be used. Twelve blades are advantageously used, however, because more or fewer can increase noise during operation. In some embodiments, the blades can have a curved surface instead of the flat surface 114. Additionally, the interior of the shaft 100 can engage the bit 92 with an interference fit, or an adjustable gripping mechanism.

With reference to FIGS. 9 and 10, the distance between the tip of a blade 96 edge and the inner wall of the head 90 can be reduced to decrease the maximum required size of the head 90. Preferably, as little as 0.010" can be the distance, though a greater or smaller distance is also possible.

With continued reference to FIGS. 7-12, the impeller assembly 110 can be generally cylindrical, with the outside diameter of the bearings 98 approximately equal to that of the impeller blades 96, thereby minimizing the size of the head 90 required to enclose the entire assembly 110. This is advantageous because a smaller head 90 size results in a more comfortable fit in a patient's mouth. The cavity housing the impeller assembly 110 can be referred to as the impeller chamber 120, and includes the space around the impeller assembly 110, into which air can be introduced.

With continued reference to FIGS. 8B, 8C, and 10, at least one edge of the flow deflector 30, when assembled, forms part of an angled nozzle entry area 112 into the head 90 from the body 50 for fluid passing through the body 50. For example, and as illustrated in FIGS. 8B and 8C, the flow deflector 30 can sit tightly within the left shell 56. An end of the flow deflector 30 can form part of the nozzle entry area 112 along the side of the head portion 90 of the left shell 56. With reference to FIG. 8C, the nozzled entry area 112 can have a rectangular cross section. This nozzle shape creates airflow that closely matches the rectangular cross-section of the turbine blades 96 and allows the incoming airflow to bear uniformly on the rectangular shaped turbine blades 96, thereby enhancing turbine power, torque and cutting effectiveness. By way of specific example, in one embodiment the rectangular nozzle is sized 0.035" high by 0.080" wide. The longer side of this rectangle coincides with the longer side of the rectangular cross section of the turbine blade 96. The nozzle size and shape can be varied from these dimensions to adjust power and torque. For example, in some embodiments the nozzle shape can be square, or have other shapes and sizes.

With continued reference to FIG. 10, the flow deflector 30 causes the airflow to enter through the nozzled entry area 112. The nozzled entry area 112 is narrower than the area preceding it in the air flow path, and directs the incoming fluid 150 to enter the head 90 at an oblique angle. In some embodiments, the deflector 30 causes fluid to enter the impeller chamber 120 in an angle approximately tangential to the impeller shaft 100. Accordingly, as fluid enters the chamber 120, the amount of momentum lost due to redirection around the perimeter of the chamber 120 is reduced. Thus, the angling caused by the deflector 30 can result in increased momentum transfer to the impeller assembly 110. Additionally, the nozzled entry area 112 can be narrower than the immediately preceding and following spaces along the air path, denoted by the arrows at 150, 152. Thus, the entry 112 can form a venturi, increasing air speed as air is passed through the nozzled entry area 112. Air circulates around the head 90 and exits through the exhaust 116, as outgoing fluid 152, back into the body 50. Preferably, the exhaust 116 is wider than the nozzled entry area 112 to inhibit back pressure.

Figure 12:
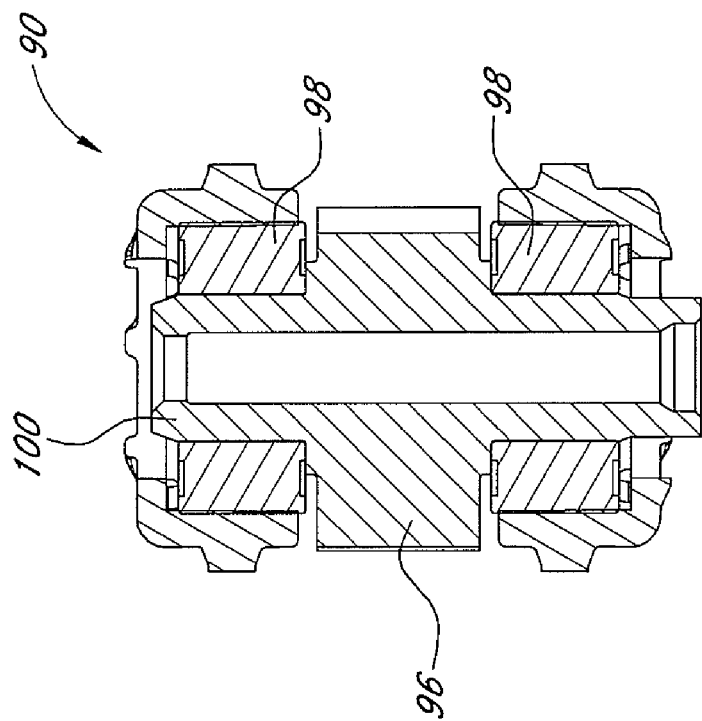
FIG. 12 is a cross sectional view of the embodiment of FIG. 11.
Figure 11:
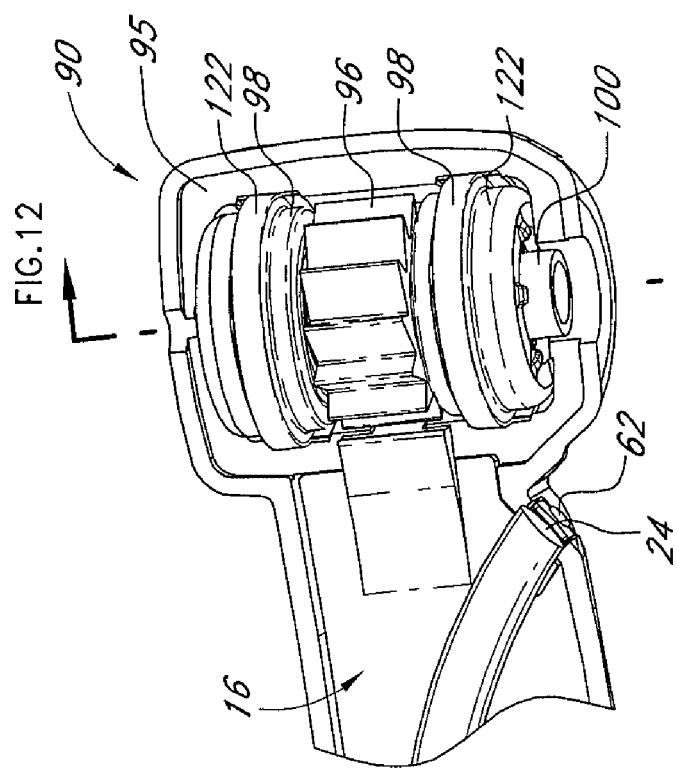
FIG. 11 is a right side elevational view of an embodiment of a dental instrument with the right shell half removed.

FIGS. 11 and 12 illustrate an embodiment of the handpiece 10 where the bit 92 has been removed. With reference to FIGS. 11 and 12, a user can remove the bit 92 and replace it with a differently sized or shaped bit, or simply replace a worn bit. For example, and with reference to FIGS. 1 and 5, the opening 94 on top of the head 90 can be used for bit removal. An object or device can be used to push through the opening 94 and force the bit out of the instrument. Preferably, the interference fit retaining the bit 92 can accommodate 3-4 changes before degrading. In some embodiments, more changes can be accommodated, the number of changes limited only by the securing of the interference fit.

Figure 13:
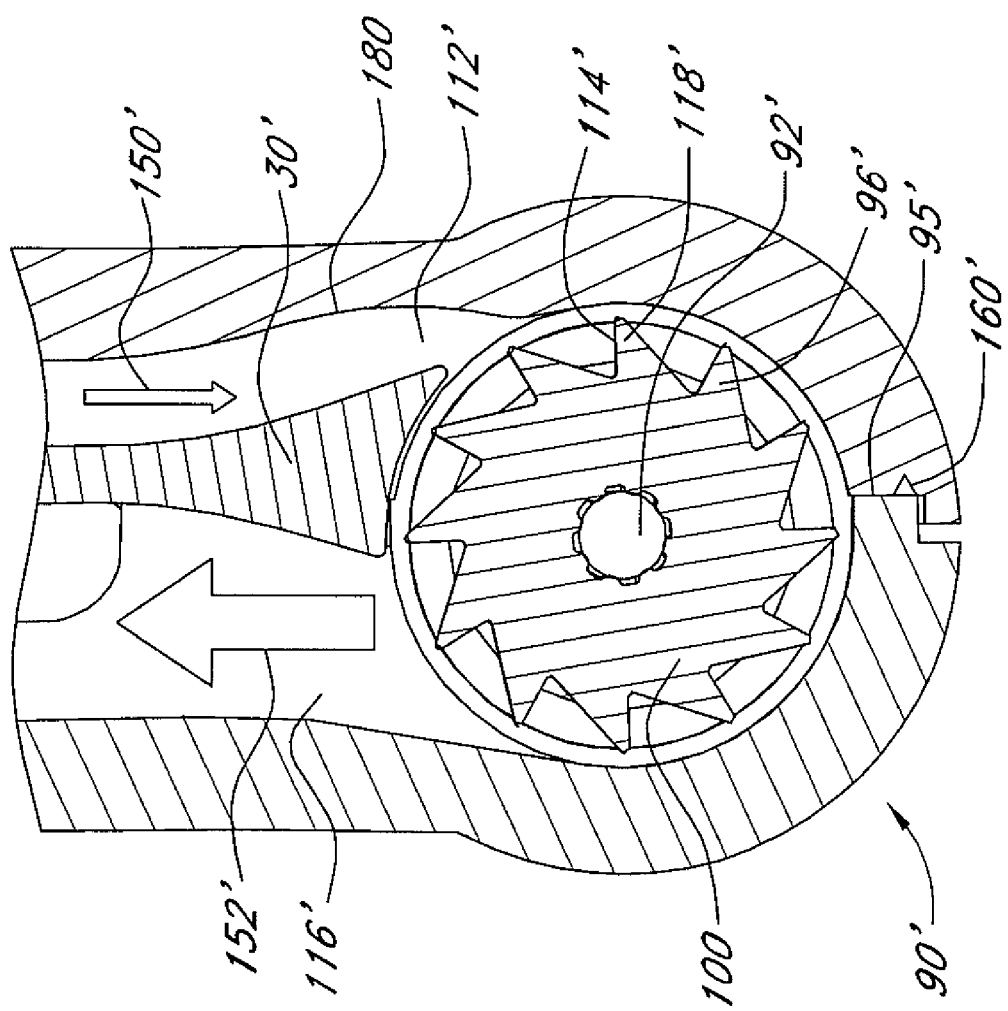
FIG. 13 is a cross sectional view of an embodiment of a head of a dental instrument.

FIG. 13 illustrates an alternative embodiment of the airflow shown in FIG. 10. A prime symbol (') has been added to the component number. With reference to FIG. 13, the nozzled entry area 112', while still forming a venturi, has a wider shape, wherein the outer wall 180 is thinned, resulting in a wider segment through which the incoming fluid 150' passes immediately prior to the nozzled entry area 112'. The wider segment is formed without altering the shape of the deflector 30'. In other embodiments, a wider or narrower entry can be used.

Although the nozzled entry area 112' has been widened, the air impacting the impeller blades 96' can arrive at the surface 114' of the blade 96' at the same angle. Thus, the substantially-tangential flow of air can be unchanged by the wider nozzled entry area 112'. In other embodiments, the shape of the entry can be altered sufficiently to redirect the flow of air away from a substantially-tangential course as well, including pointing further inward toward the center of the impeller assembly, or towards the inner wall, away from the center of the assembly.

Figure 14:
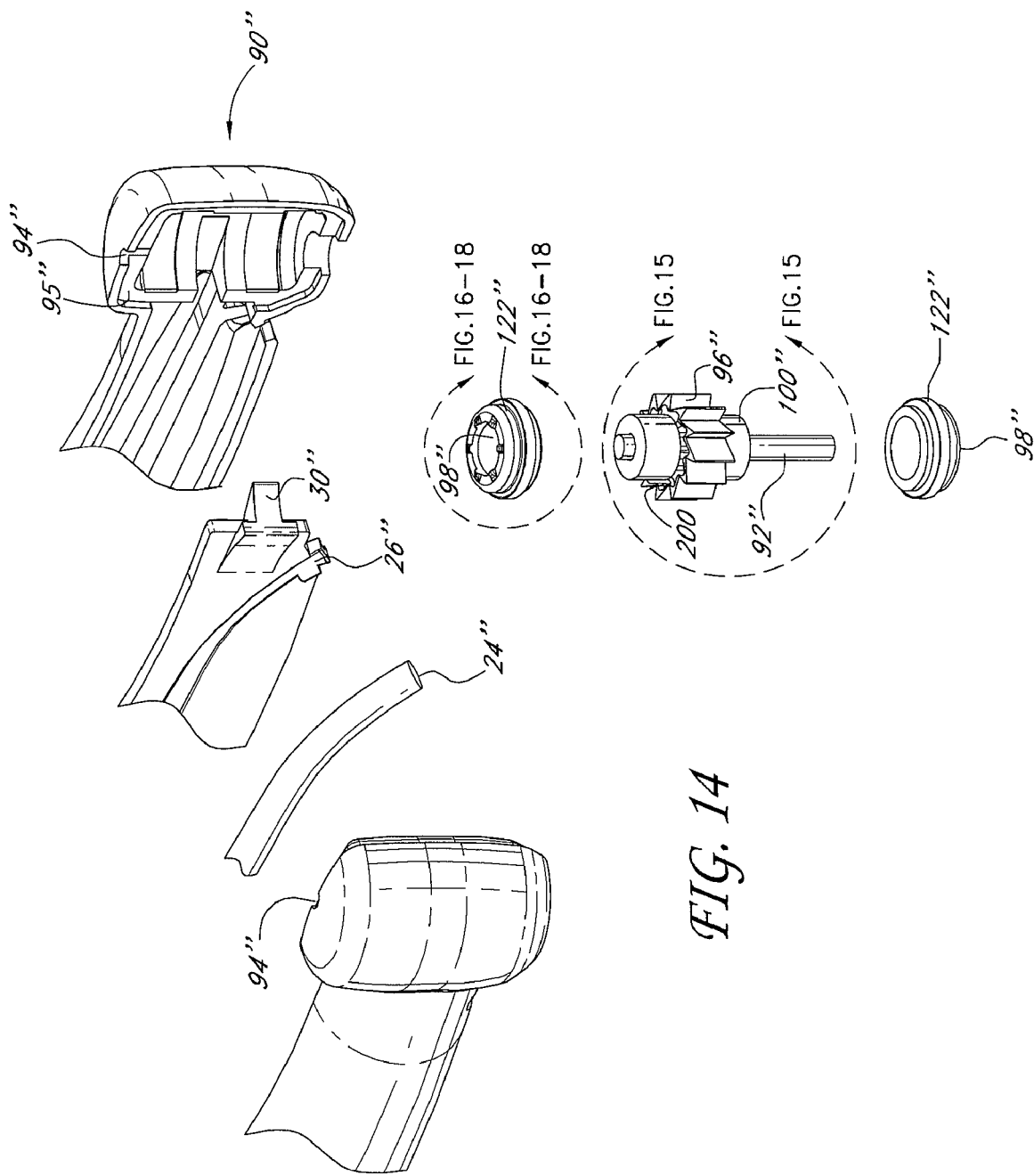
FIG. 14 is an exploded perspective view of an embodiment of a dental instrument.
Figure 15B:
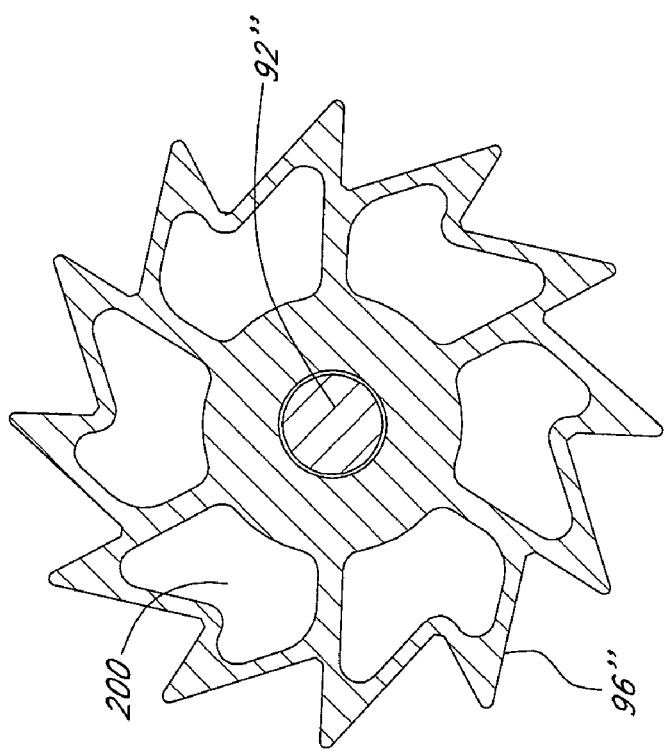
FIG. 15B is a cross sectional view of the embodiment of FIG. 15A.
Figure 15A:
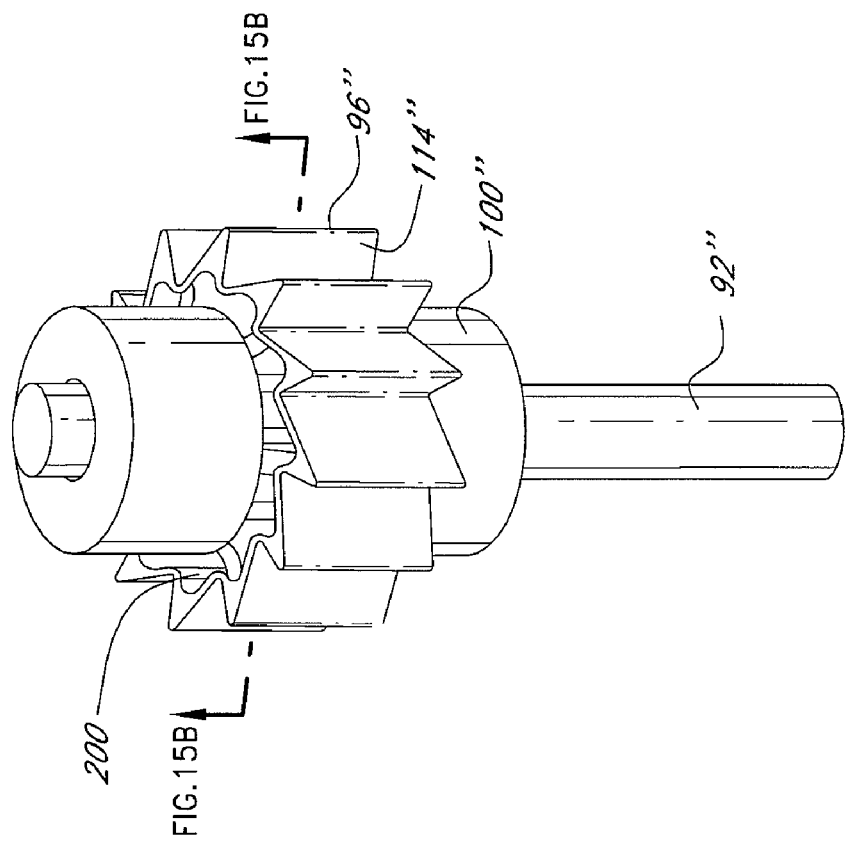
FIG. 15A is a front and top side perspective view of an embodiment of the turbine impeller components of a dental instrument.

FIGS. 14, 15A, and 15B illustrate embodiments of a handpiece 10 wherein the components are substantially similar to those described above in FIG. 2 and 13, except that a double prime symbol (") has been added to the number. FIG. 14 illustrates a detailed view of the head of an exploded embodiment of a handpiece. FIG. 15A illustrates a detailed view of the turbine, while FIG. 15B shows a cross-section of the turbine. With reference to FIGS. 14, 15A, and 15B, the turbine shaft 100" can extend radially outward to form the impeller blades 96". In some embodiments, such as the one shown in FIG. 2, the blades 96 can be solid portions of the material forming the shaft. By contrast, and with reference to FIGS. 14, 15A, and 15B, cavities 200 can be formed within the outer boundary of the blades 96", lowering the weight of the turbine shaft/blade unit 96", 100". Lowering the weight can reduce cost, and make the handpiece 10 easier to ship and handle. Additionally, although six cavities are shown, more or fewer can be used, and they can have different shapes, including but not limited to cylindrical or rectangular prisms. In some embodiments, the cavities 200 can occupy more or less space, creating for example a nearly completely solid shaft 100", or a shaft having a plurality of voids which remove a large portion of the shaft material without compromising the strength of the shaft 100".

Figure 15C:
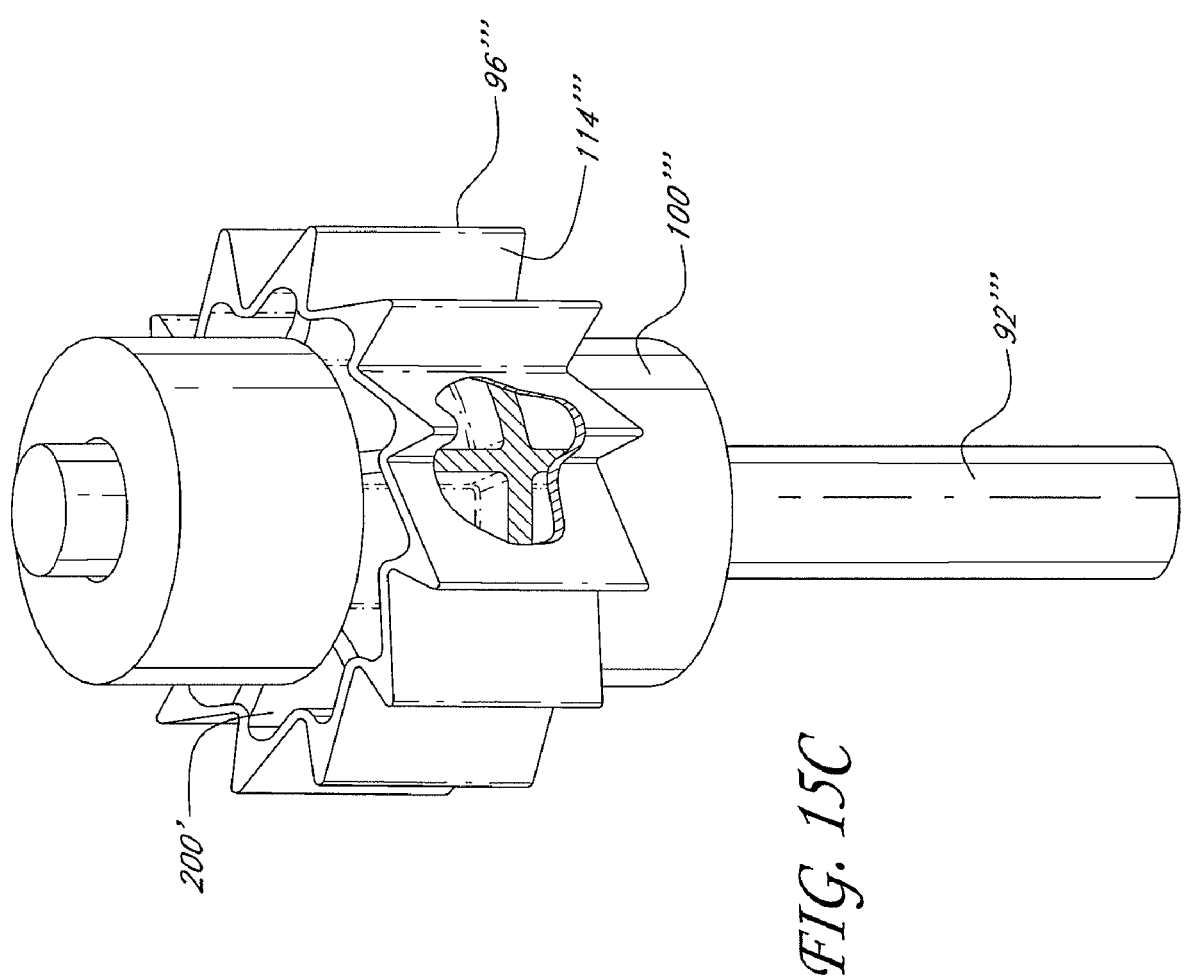
FIG. 15C is a front and top side perspective view of an embodiment of the turbine impeller components of a dental instrument.

FIG. 15C illustrates another embodiment of the turbine with components substantially similar to those described above in FIGS. 2, 13, 14, 15A, and 15B, except that a triple prime symbol ("')has been added to the number. As described above, cavities 200''' can be formed within the outer boundary of the blades 96''' having a variety of shapes. With reference to FIG. 15C, the cavities 200''' are present as material missing from portions of the turbine shaft 100'''. Some material remains between cavities 200''', however, forming a boundary between them. Other variations of cavity construction, size, and shape are also possible.

Figure 16B:
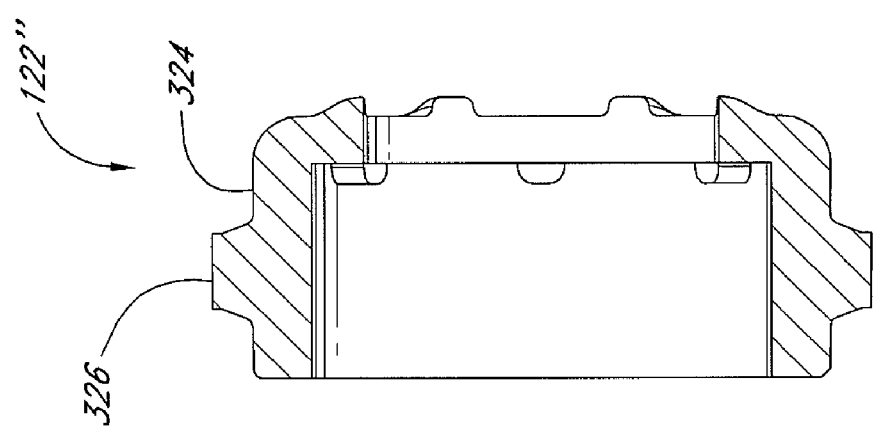
FIG. 16B is a cross sectional view of the embodiment of FIG. 16A.
Figure 16A:
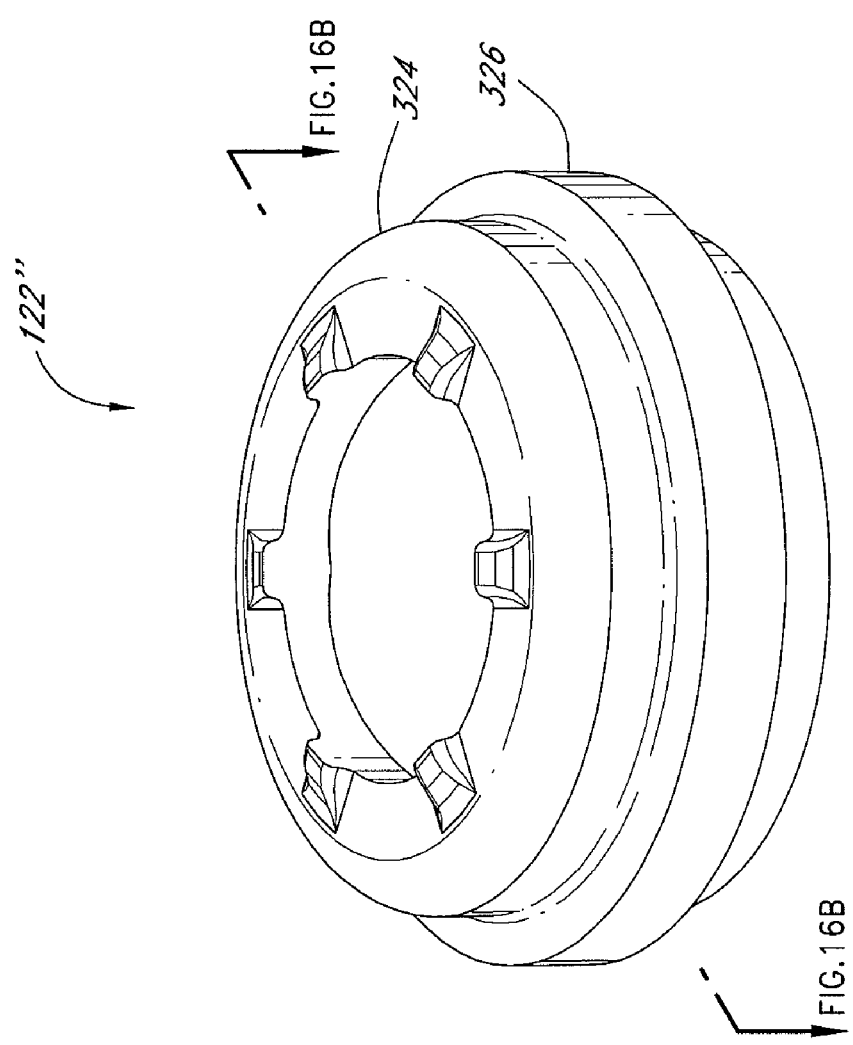
FIG. 16A is a front and top side perspective view of an embodiment of a grommet as used in a dental instrument.

With reference to FIGS. 16A and 16B, other types or variations of grommets can be used in a handpiece. For example, and with reference to FIGS. 16A and 16B, a grommet 122" has a protruding ring or rib 326 on the outer surface 324 of the grommet 122". The rib 326 can extend from the portion of the outer surface 324 as illustrated, or be of a different width or extend a greater or lesser distance from the surface 324. The rib 326 provides an interface surface, increasing the friction between the grommet 122" and the inner surface of the handpiece 10, thereby helping the grommet 122" retain its position.

Figure 17B:
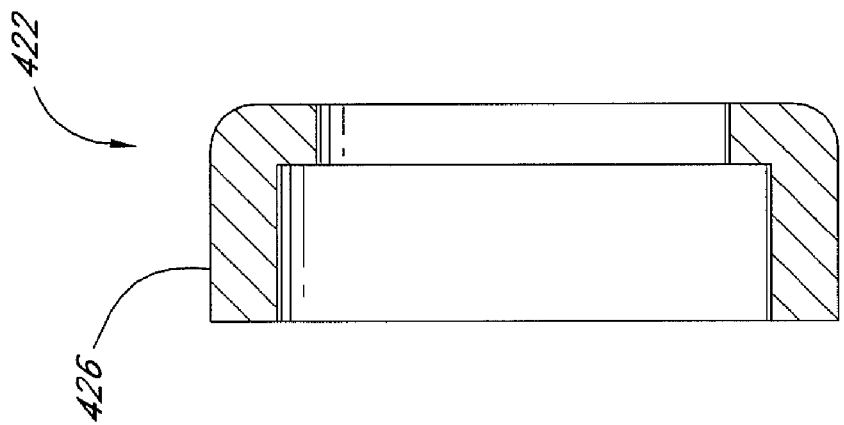
FIG. 17B is a cross sectional view of the embodiment of FIG. 17A.
Figure 17A:
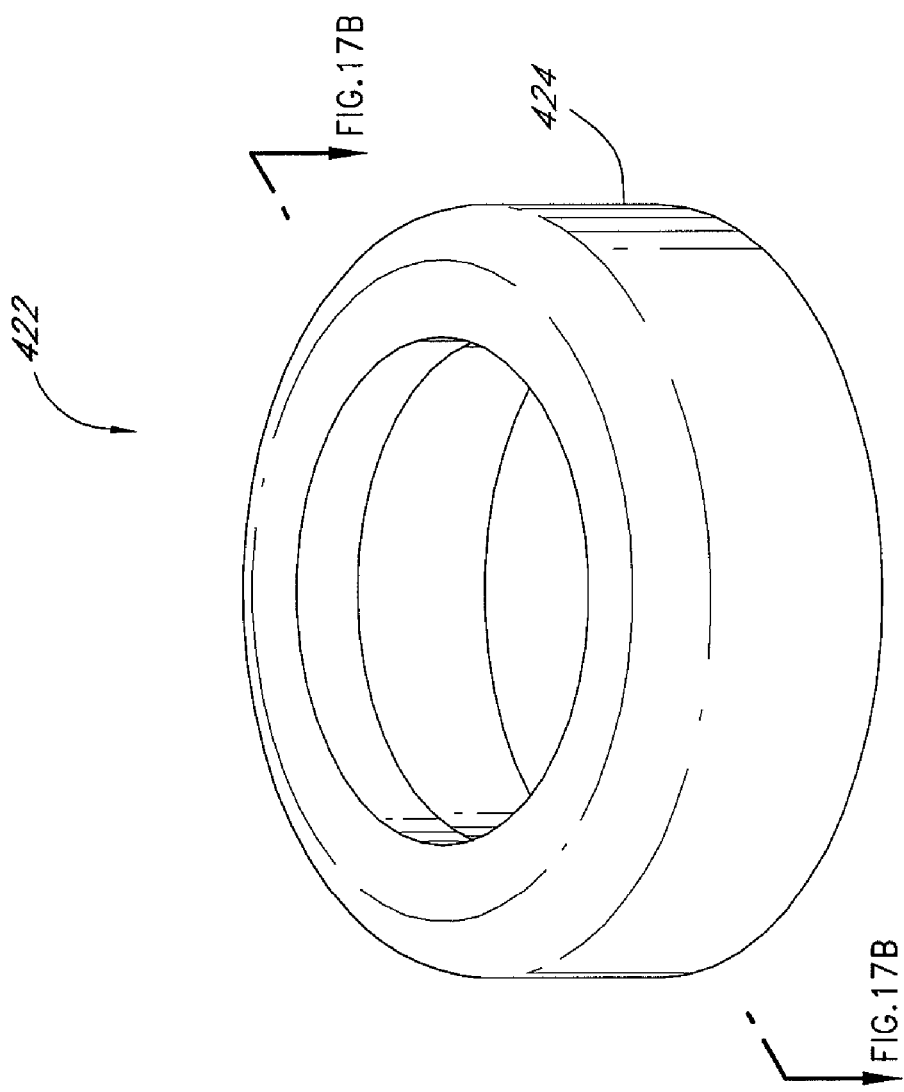
FIG. 17A is a front and top side perspective view of an embodiment of a grommet as used in a dental instrument.

FIGS. 17A and 17B illustrate yet another embodiment of a grommet 422 which can be used with the handpiece 10. With reference to FIGS. 17A and 17B, the grommet 422 has no rib along outer surface 424.

Figure 18B:
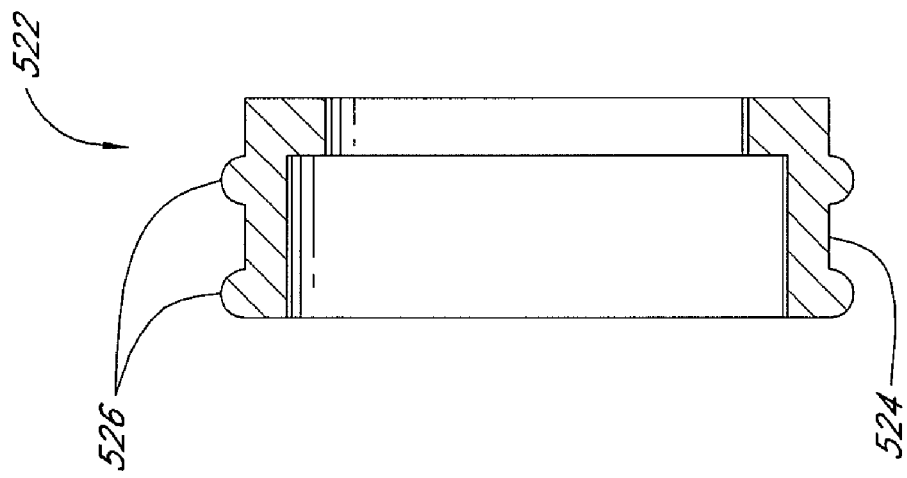
FIG. 18B is a cross sectional view of the embodiment of FIG. 18A.
Figure 18A:
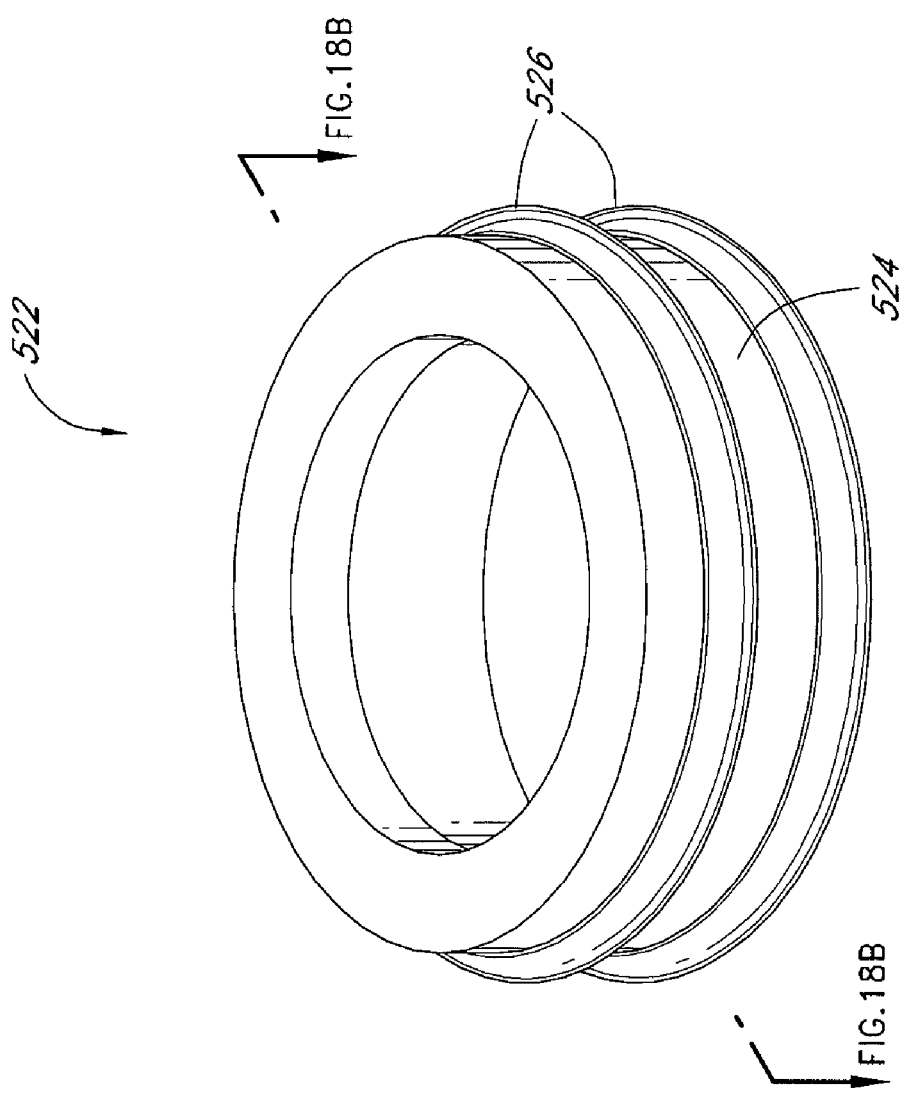
FIG. 18A is a front and top side perspective view of an embodiment of a grommet as used in a dental instrument.

FIGS. 18A and 18B illustrate yet another embodiment of a grommet 522 which can be used with the handpiece 10. With reference to FIGS. 18A and 18B, the grommet 522 comprises two ribs 526 along outer surface 524. Adding a second rib to the grommet can help reduce the aubible noise coming from the handpiece 10. More ribs can also be used. The outer surface of the ribs can be flat and smooth, as illustrated in Figures 16A and 16B, rounded, as illustrated in FIGS. 18A and 18B, or they can have surface features, such as scoring or adhesives, to assist in retaining the position of the grommet. Other cross-sectional shapes can also be used, including but not limited to triangular or serrated.

Assembly

Prior to assembly, central core 16 and base portion 11, and the right and left shells 54, 56 can be created from single-gate injection molding. The light pipe 18, and impeller blade/shaft turbine 96, 100 can be formed from injection molding as well. Preferably, the impeller blade/shaft turbine 96, 100 is formed from multi-gated molding to produce a balanced turbine. The number of gates for injection molding the impeller blade/shaft turbine 96,100 can be as few as 1, though preferably more. Any number of gates, including, without limitation, two, four, eight, twelve, or more can be used. For the shells 54, 56, center core 16 and base 11, and turbine 96, 100, ABS is preferably used to simplify manufacturing, though other plastics can be used.

Although ABS is used in some embodiments to facilitate ultrasonic welding, other methods of assembly, including without limitation, glues, heat sealing, thermal welding, other sonic welding, or mechanical fixtures such as screws can also be used to form components. Accordingly, other plastics can be used as appropriate for the material and cost requirements. One such example is a polyetherimide thermoplastic resins, which can include the commercial compound Ultem™.

During assembly of the impeller assembly 110, the center core 16 and coupled base 11 can be preferably placed atop the left shell 56, preferably aligning and coupling the seam 33 with the taper portion 60, and the protrusions 38 with the mating surfaces 61. The center core 16 can then be welded to the left shell 56. The light pipe 16 can then be disposed in one of the conduits 14 of the base 11 and engage the molded projections 22, with a second end 24 positioned at or near the light exit port 26. The impeller assembly 110 can then be assembled. The bearings 98 can be disposed around the turbine 96, 100 and coupled thereto. After the bearings are pressed onto the turbine, the grommets 122 are installed over the bearings. The impeller 110 can then be placed in the head 90. Subsequently, the protrusions 70 of the right shell 54 can be aligned with the flat face and mating area 19 along the core 16, as well as the flat mating surfaces 95 in the head region, and the right shell 54 can be welded to the core 16, closing the body 50.

Following assembly, the packaged handpiece 10 can be sterilized by exposure to ethylene oxide (EtO) gas, gamma rays, or electrons from an electron gun. EtO gas advantageously does not discolor plastic and is the preferred, but not exclusive, method of sterilization. Some embodiments of the handpiece 10 are packaged in a gas-permeable material, which inhibits the passage of pathogens through the material. After enclosure, the package can be exposed to EtO gas, which can sterilize the handpiece within the package and the surfaces of the package simultaneously. The handpieces 10 can then be shipped and stored.

Operation

The handpiece 10 is typically coupled with a fluid source providing air, water, and light to the conduits 14. Specifically, pressurized air can be provided to the conduit designated 64, light to the conduit designated 68, a vent can be coupled to the conduit designated 66, and a source providing water or pressurized water can be coupled to a conduit located beneath the wall 58. Thus, during use, light can be provided through the light pipe 18 to a point along or near the bit 92. Similarly, water can be selectively dispensed through the portion of the body 50 beneath the wall 58 and out the fluid port 62 to a point along or near the bit 92. In some embodiments, air is provided instead of water. Either can be used to clear tooth and other debris from the working area of the bit 92, as well as cool the portion of the tooth being drilled and the drill bit. Control can be exerted by the operator over the fluid source to control the use of water, air, and light.

During operation of the handpiece 10, pressurized air is provided from the fluid source to the conduit 64. This air travels through one side of the body 50 having an interior surface which is advantageously smooth to reduce friction. The air is then directed by the flow deflector 30 to a direction substantially tangential to the circular shape formed by the impeller assembly 110, particularly, the impeller blades 96. Thus, as the air passes through the nozzle entry area 112, it is directed to impact an engagement surface 114 of at least one of the blades 96. Air can be angled to preferably impact the flat surface 114 of an impeller blade 96 as the flat surface 114 is oriented along a line extending from the center of axis of rotation radially towards the exterior of the head, as shown in FIG. 10. Advantageously, the impeller blade 96 is rotated in the direction of air flow, causing the shaft 100 and coupled bit 92 to rotate. Preferably, the bearings 98 allow the shaft 100 to rotate smoothly, in a stable position, and quietly at high speed.

Maximum power is typically achieved at approximately 50% of the free running rpm of the handpiece 10. The handpiece 10 can reach rotational speeds as high as 280,000 to 400,000 rpm when pressurized air of approximately 35 to 40 p.s.i. is supplied. Pressurized air preferably can be provided at approximately 40 p.s.i., though other pressures, for example as low as 15 p.s.i. or as high as 45 p.s.i. can also be used. Preferably, the handpiece 10 is operated at speeds of at least 160,000 rpm when coupled with an ISO-compliant source of pressurized air and light. In some embodiments, it has been found that the handpiece can have power equal to or greater than some of the leading metal reusable handpieces against which the embodiments were benchmarked. The speed at which peak power occurs is approximately one half of the free running rpm, although it could be more or less, depending on operating conditions and changes to the handpiece. Preferably, the handpiece 10 is operated to produce a noise level as low as possible. By way of specific examples, the noise level range is typically between 55 and 65 decibels. A noise level as low as 53 decibels has been observed. In certain embodiments, the noise level can be greater than 65 decibels as well.

After use on a single patient, the disposable dental handpiece 10 can be discarded, removing the need to re-sterilize it for the next patient. The foregoing description is that of preferred constructions having certain features, aspects, and advantages. However changes and modifications may be made to the above-described arrangements without departing from the spirit and scope of the invention. As one example, a hollow turbine having twelve straight blades made from four-gate injection molding can be used in one embodiment, while a solid turbine having eight curved blades made from two-gate injection molding can be used in another embodiment. In another example, either turbine could be disposed in a handpiece having a nozzle inlet such as that disclosed in FIG. 10, or either turbine could be disposed in a handpiece having a nozzle inlet such as that disclosed in FIG. 13. Other combinations and permutations of the features described above are possible as well.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combinations or sub-combinations of the specific features and aspects of the embodiments can be made and still fall within the scope of the inventions. It should be understood that various features and aspects of the disclosed embodiments can be combined with or substituted for one another in order to form varying modes of the disclosed inventions. Thus, it is intended that the scope of at least some of the present inventions herein disclosed should not be limited by the particular disclosed embodiments described above.

What is claimed is:

1. A dental instrument driven by compressed air comprising:
    an elongated body comprising:
        a first shell half, a second shell half, and a core, the shell halves joined to form an exterior surface for manual manipulation, the halves forming a cavity, the cavity comprising various passageways as fluid conduits;
        a base comprising a plurality of conduits, the base communicating with an outside source of light and fluid through the conduits, the conduits communicating with the passageways defined by the elongated body;
        a head located at the opposite end from the base, the head comprising a turbine shaft rotatably mounted within the head, a turbine impeller, the turbine impeller connected to the turbine shaft, the turbine impeller being driven by an outside source of air through an air nozzle to rotate a dental bit;
    at least one opening located under the head configured to deliver fluid away from the dental instrument; and
    at least one opening located under the head configured to deliver light away from the dental instrument, wherein the core comprises a flow deflector located on the end of the core nearest the head, the flow deflector projecting further towards the first shell half than towards the second shell half, an edge of the flow deflector forming a part of the nozzle, and wherein the flow deflector comprises protrusions on upper and lower portions of the flow deflector, the protrusions configured to mate the flow deflector and core to the first shell half.

2. The dental instrument of claim 1, wherein the shape of the flow deflector causes incoming fluid to enter the head of the handpiece at an oblique angle.

3. The dental instrument of claim 1, wherein the flow deflector causes fluid to enter the nozzle at an angle approximately tangential to the turbine shaft.

4. The dental instrument of claim 1, wherein the entry of air into the head through the nozzle is narrower than the immediately preceding and following spaces along an air path through the handpiece.

5. The dental instrument of claim 1, wherein the flow deflector and nozzle form a venturi which increases the air speed as the air is passed through the head.

6. The dental instrument of claim 1, wherein the dental instrument is disposable, sterile prior to use, and substantially maintenance free.

7. The dental instrument of claim 1, comprising an air path where air circulates around the head and exits through an exhaust area as outgoing fluid back into the body.

8. The dental instrument of claim 7, wherein the exhaust area is larger than the area of the nozzle.

9. The dental instrument of claim 1, further comprising grommets, wherein the turbine shaft is mounted within the head using the grommets, and wherein the grommets include at least one circumferential rib along outer surfaces of the grommets.

10. The dental instrument of claim 1, wherein the dental instrument is plastic.

* * * * *